United States Patent
Gavney, Jr.

(10) Patent No.: US 7,877,833 B2
(45) Date of Patent: Feb. 1, 2011

(54) ORAL-CARE DEVICE AND SYSTEM

(76) Inventor: James A. Gavney, Jr., 725 Wildwood La., Palo Alto, CA (US) 94303

( * ) Notice: Subject to any disclaimer, the term of this patent is extended or adjusted under 35 U.S.C. 154(b) by 1018 days.

(21) Appl. No.: 11/176,775

(22) Filed: Jul. 6, 2005

(65) Prior Publication Data

US 2006/0236477 A1    Oct. 26, 2006

Related U.S. Application Data

(63) Continuation-in-part of application No. 10/839,988, filed on May 5, 2004, now Pat. No. 6,944,903, which is a continuation of application No. 10/382,559, filed on Mar. 5, 2003, now Pat. No. 6,820,299, which is a continuation of application No. 09/588,686, filed on Jun. 5, 2000, now Pat. No. 6,571,417, which is a continuation-in-part of application No. 09/330,704, filed on Jun. 11, 1999, now Pat. No. 6,319,332.

(51) Int. Cl.
*A47L 13/11* (2006.01)
(52) U.S. Cl. ............... 15/29; 15/22.1; 15/117; 15/114; 401/270
(58) Field of Classification Search ......... 15/97.1, 15/29, 28, 22.1, 117, 121, 114; 433/80, 82; 401/270, 272, 280
See application file for complete search history.

(56) References Cited

U.S. PATENT DOCUMENTS

| | | |
|---|---|---|
| 915,251 A | 3/1809 | Vanderslice |
| 620,151 A | 3/1849 | Emsa-Works et al. |
| 34,109 A | 1/1862 | Fenshaw et al. |
| 66,834 A | 7/1867 | Harlan |
| 104,886 A | 6/1870 | Rhodehamel |
| 116,030 A | 6/1871 | Devines |
| 116,346 A | 6/1871 | O'Brian |
| 214,701 A | 4/1879 | Dessau |
| 218,431 A | 8/1879 | Dunham |
| 290,515 A | 12/1883 | Voltz et al. |
| 305,735 A | 9/1884 | Leeson et al. |
| 411,910 A | 10/1889 | Van Horne |

(Continued)

FOREIGN PATENT DOCUMENTS

| | | |
|---|---|---|
| CH | 172320 | 12/1934 |
| DE | 31 14 507 A1 | 3/1983 |
| DE | 298 16 488 U1 | 1/1999 |
| DE | 199 57 639 A1 | 6/2001 |
| EP | 0 435 329 A2 | 9/1989 |
| EP | 0 360 766 A1 | 3/1990 |
| FR | 2 636 818 | 3/1990 |
| FR | 2 793 136 | 11/2000 |

(Continued)

OTHER PUBLICATIONS

"A new high-performance manual toothbrush" Supported by the Colgate-Palmolive Company, 2004 Medical World Business Press, Inc.

(Continued)

*Primary Examiner*—Shay L Karls
(74) *Attorney, Agent, or Firm*—JAG Patent Services LLC; James A. Gavney, Jr.

(57) ABSTRACT

An oral-care device with a power cleaning head configured to dispense an oral-care cleaning solution is disclosed. The power cleaning head comprises squeegees and bristles and one or more apertures for dispensing the oral-care solution. Preferably, the squeegee and bristle are configured to rotate, oscillate, vibrate or otherwise move while dispensing the oral-care solution through the one or more apertures.

23 Claims, 13 Drawing Sheets

U.S. PATENT DOCUMENTS

| | | | |
|---|---|---|---|
| 742,639 A | 10/1903 | Harlan | |
| 907,842 A | 12/1908 | Meuzies | |
| 1,006,630 A | 10/1911 | Clarke | |
| 1,128,139 A | 2/1915 | Hoffman | |
| 1,142,698 A | 6/1915 | Grove et al. | |
| 1,188,823 A | 6/1916 | Plank | |
| 1,191,556 A | 7/1916 | Blake | |
| 1,268,544 A | 6/1918 | Cates | |
| 1,297,272 A | 3/1919 | Strang et al. | |
| 1,405,279 A | 1/1922 | Cassedy | |
| 1,500,274 A | 7/1924 | Scarling | |
| 1,526,267 A | 2/1925 | Dessau | |
| 1,578,074 A | 3/1926 | Chandler | |
| 1,588,785 A | 6/1926 | Van Sant | |
| 1,598,224 A | 8/1926 | Van Sant | |
| 1,705,249 A | 3/1929 | Henry | |
| 1,707,118 A | 3/1929 | Goldberg | |
| 1,720,017 A | 7/1929 | Touchstone | |
| 1,766,529 A | 6/1930 | Peirson | |
| 1,833,555 A | 11/1931 | Bell et al. | |
| 1,852,480 A | 4/1932 | Ruetz | |
| 1,868,893 A | 7/1932 | Gentle | |
| 1,910,414 A | 5/1933 | Varga | |
| 1,924,152 A | 8/1933 | Coney et al. | 15/167 |
| 1,965,009 A | 7/1934 | Stevens | 15/188 |
| 1,993,662 A | 3/1935 | Green | 15/110 |
| 1,993,763 A | 3/1935 | Touchstone | 15/180 |
| 2,008,636 A | 7/1935 | Brynan | 91/67.4 |
| 2,042,239 A | 5/1936 | Planding | 15/110 |
| 2,059,914 A | 11/1936 | Rosenberg | 15/110 |
| 2,088,839 A | 8/1937 | Coney et al. | 15/188 |
| 2,117,174 A | 5/1938 | Jones | 15/110 |
| 2,129,082 A | 9/1938 | Byrer | 128/62 |
| 2,139,245 A | 12/1938 | Ogden | 128/62 |
| 2,144,408 A | 1/1939 | Holmes | 128/62 |
| 2,154,846 A | 4/1939 | Heymann et al. | 128/62 |
| 2,164,219 A | 6/1939 | McGerry | 128/62 |
| 2,219,753 A | 10/1940 | Seguin | 15/188 |
| 2,226,145 A | 12/1940 | Smith | 15/29 |
| 2,244,699 A | 6/1941 | Hosey | 15/188 |
| 2,279,355 A | 4/1942 | Wilensky | 15/110 |
| 2,312,828 A | 3/1943 | Adamsson | 15/167 |
| 2,321,333 A | 6/1943 | Terry | 15/135 |
| 2,334,796 A | 11/1943 | Steinmetz et al. | 15/121 |
| 2,443,461 A | 6/1948 | Kempster | 15/188 |
| 2,516,491 A | 7/1950 | Swastek | 15/188 |
| 2,518,765 A | 8/1950 | Ecker | 15/115 |
| 2,534,086 A | 12/1950 | Vosbikian et al. | 15/245 |
| 2,545,814 A * | 3/1951 | Kempster | 15/188 |
| 2,587,382 A | 2/1952 | Pyne | 15/136 |
| 2,637,870 A | 5/1953 | Cohen | 15/188 |
| 2,644,974 A | 7/1953 | Anderson | 15/121 |
| 2,702,914 A | 3/1955 | Kittle et al. | 15/114 |
| 2,715,745 A | 8/1955 | Jacobsen | 15/121 |
| 2,757,668 A | 8/1956 | Meyer-Saladin | 128/173.1 |
| 2,807,820 A | 10/1957 | Dinhofer | 15/176 |
| 2,815,601 A | 12/1957 | Hough, Jr. | 41/5.5 |
| 2,875,458 A | 3/1959 | Tsuda | 15/22 |
| 2,884,151 A | 4/1959 | Biederman | 215/41 |
| 2,946,072 A | 7/1960 | Filler et al. | 15/110 |
| 2,987,742 A | 6/1961 | Kittle et al. | 15/114 |
| 3,103,027 A | 9/1963 | Birch | 15/110 |
| 3,110,052 A | 11/1963 | Whitman | 15/117 |
| 3,133,546 A | 5/1964 | Dent | 132/120 |
| 3,181,193 A | 5/1965 | Nobles et al. | 15/114 |
| 3,195,537 A | 7/1965 | Blasi | 128/56 |
| 3,230,562 A | 1/1966 | Birch | 15/110 |
| 3,231,925 A | 2/1966 | Conder | 15/605 |
| 3,261,354 A | 7/1966 | Shpuntoff | 128/173 |
| 3,359,588 A | 12/1967 | Kobler | 15/110 |
| 3,400,417 A | 9/1968 | Moret | 15/22 |
| 3,491,396 A | 1/1970 | Eannarino et al. | 15/104.94 |
| 3,553,759 A | 1/1971 | Kramer et al. | 15/110 |
| 3,563,233 A | 2/1971 | Bodine | 128/36 |
| 3,570,726 A | 3/1971 | Pomodoro | 222/546 |
| 3,641,610 A | 2/1972 | Lewis, Jr. | 15/114 |
| 3,939,522 A | 2/1976 | Shimizu | 15/244 R |
| 3,969,783 A | 7/1976 | Shipman | 15/250.04 |
| 3,977,084 A | 8/1976 | Sloan | 32/59 |
| 3,992,747 A | 11/1976 | Hufton | 15/321 |
| 4,090,647 A | 5/1978 | Dunning | 222/543 |
| 4,115,893 A | 9/1978 | Nakata et al. | 15/110 |
| 4,128,910 A | 12/1978 | Nakata et al. | 15/110 |
| 4,167,794 A | 9/1979 | Pomeroy | 15/188 |
| 4,277,862 A | 7/1981 | Weideman | 15/110 |
| 4,288,883 A | 9/1981 | Dolinsky | 15/110 |
| 4,428,091 A | 1/1984 | Janssen | 15/167 A |
| 4,458,374 A | 7/1984 | Hukuba | 15/22 R |
| 4,573,920 A | 3/1986 | d'Argembeau | 433/141 |
| 4,585,416 A | 4/1986 | DeNiro et al. | 433/140 |
| 4,610,043 A | 9/1986 | Vezjak | 15/111 |
| 4,619,009 A * | 10/1986 | Rosenstatter | 15/29 |
| 4,691,405 A | 9/1987 | Reed | 15/201 |
| 4,727,986 A | 3/1988 | Feldstein | 206/229 |
| 4,763,380 A | 8/1988 | Sandvick | 15/160 |
| 4,812,070 A | 3/1989 | Marty | 401/289 |
| 4,827,551 A | 5/1989 | Maser et al. | 15/24 |
| 4,866,806 A | 9/1989 | Bedford | 15/104.94 |
| 4,887,924 A | 12/1989 | Green | 401/261 |
| 4,913,133 A | 4/1990 | Tichy | 128/62 |
| 4,929,180 A | 5/1990 | Moreschini | 433/166 |
| 5,005,246 A | 4/1991 | Yen-Hui | 15/111 |
| 5,032,082 A | 7/1991 | Herrera | 433/141 |
| 5,040,260 A | 8/1991 | Michaels | 15/167.1 |
| D326,019 S | 5/1992 | Spangler et al. | D4/118 |
| 5,186,627 A * | 2/1993 | Amit et al. | 433/216 |
| 5,211,494 A | 5/1993 | Baijnath | 401/28 |
| 5,226,197 A | 7/1993 | Nack et al. | 15/111 |
| 5,249,327 A | 10/1993 | Hing | 15/104.94 |
| 5,283,921 A | 2/1994 | Ng | 15/22.1 |
| 5,289,605 A | 3/1994 | Armbruster | 15/97.1 |
| 5,309,590 A * | 5/1994 | Giuliani et al. | 15/22.1 |
| 5,335,389 A | 8/1994 | Curtis et al. | 15/167.1 |
| 5,341,537 A | 8/1994 | Curtis et al. | 15/167.1 |
| 5,429,678 A | 7/1995 | Fany | 134/6 |
| 5,438,726 A | 8/1995 | Leite | 15/105 |
| 5,491,863 A | 2/1996 | Dunn | 15/106 |
| 5,528,793 A | 6/1996 | Schbot | 15/245 |
| 5,535,474 A | 7/1996 | Salazar | 15/110 |
| 5,584,690 A | 12/1996 | Maassarani | 433/125 |
| 5,604,951 A * | 2/1997 | Shipp | 15/167.1 |
| 5,615,449 A | 4/1997 | Sepke | 15/322 |
| 5,628,082 A | 5/1997 | Moskovich | 15/110 |
| 5,669,097 A | 9/1997 | Klinkhammer | 15/167.1 |
| 5,689,850 A | 11/1997 | Shekalim | 15/22.1 |
| 5,711,759 A | 1/1998 | Smith et al. | 601/139 |
| 5,735,011 A | 4/1998 | Asher | 15/167.1 |
| 5,799,353 A | 9/1998 | Oishi et al. | 15/167.1 |
| 5,802,656 A | 9/1998 | Dawson et al. | 15/110 |
| 5,806,127 A | 9/1998 | Samoil et al. | 15/104.94 |
| 5,810,856 A | 9/1998 | Tveras | 606/161 |
| 5,839,149 A | 11/1998 | Scheier et al. | 15/167.2 |
| D402,116 S | 12/1998 | Magloff et al. | D4/104 |
| D403,510 S | 1/1999 | Menke et al. | D4/104 |
| 5,896,614 A | 4/1999 | Flewitt | 15/167.1 |
| 5,930,860 A | 8/1999 | Shipp | 15/110 |
| 5,966,771 A | 10/1999 | Stroud | 15/117 |
| 5,970,564 A | 10/1999 | Inns et al. | 15/201 |
| 5,980,542 A | 11/1999 | Saldivar | 606/161 |
| 5,991,959 A | 11/1999 | Raven et al. | 15/201 |
| 6,000,088 A | 12/1999 | Wright et al. | 15/119.2 |
| 6,003,187 A | 12/1999 | Footer et al. | 15/119.2 |
| 6,021,541 A | 2/2000 | Mori et al. | 15/167.1 |
| 6,032,313 A | 3/2000 | Tsang | 15/22.1 |

| | | | | | | |
|---|---|---|---|---|---|---|
| 6,032,322 | A | 3/2000 | Forsline ............... 15/245.1 | 6,892,412 B2 | 5/2005 | Gatzemeyer et al. ......... 15/22.2 |
| 6,041,467 | A | 3/2000 | Roberts et al. ............. 15/167.1 | 6,938,293 B2 | 9/2005 | Eliav et al. .................... 15/22.1 |
| D422,143 | S | 4/2000 | Beals et al. .................. D4/104 | 6,983,507 B2 | 1/2006 | McDougall ................ 15/22.1 |
| 6,044,514 | A | 4/2000 | Kaneda et al. ............. 15/167.1 | 2001/0020314 A1 | 9/2001 | Calabrese ................... 15/22.1 |
| D424,808 | S | 5/2000 | Beals et al. .................. D4/104 | 2001/0039689 A1 | 11/2001 | Gavney, Jr. ................... 15/117 |
| D425,306 | S | 5/2000 | Beals et al. .................. D4/104 | 2002/0124337 A1 | 9/2002 | Calabrese et al. ............. 15/110 |
| 6,065,890 | A | 5/2000 | Weitz ........................ 401/146 | 2003/0033680 A1 | 2/2003 | Davies et al. ................. 15/22.1 |
| 6,067,684 | A | 5/2000 | Kweon ...................... 15/167.1 | 2003/0033682 A1 | 2/2003 | Davies et al. ................. 15/110 |
| 6,077,360 | A | 6/2000 | Takashima ..................... 134/6 | 2003/0182746 A1 | 10/2003 | Fattori et al. ................. 15/22.1 |
| 6,088,869 | A | 7/2000 | Kaneda et al. ............. 15/167.1 | 2003/0196283 A1 | 10/2003 | Eliav et al. .................... 15/22.1 |
| 6,092,255 | A | 7/2000 | Kim ............................ 15/121 | 2004/0010869 A1 | 1/2004 | Fattori et al. ................. 15/22.1 |
| 6,099,309 | A | 8/2000 | Cardarelli ................... 433/125 | 2004/0045105 A1 | 3/2004 | Eliav et al. .................... 15/22.1 |
| 6,108,854 | A | 8/2000 | Dingert ......................... 15/188 | 2004/0060132 A1 | 4/2004 | Gatzemeyer et al. ......... 15/22.1 |
| 6,115,871 | A | 9/2000 | Royer ........................ 15/167.2 | 2004/0060133 A1 | 4/2004 | Eliav ........................... 15/22.1 |
| 6,126,533 | A | 10/2000 | Johnson et al. .............. 451/527 | 2004/0060135 A1 | 4/2004 | Gatzemeyer et al. ......... 15/22.1 |
| 6,151,745 | A | 11/2000 | Roberts et al. ............. 15/167.1 | 2004/0060136 A1 | 4/2004 | Gatzemeyer et al. ......... 15/22.1 |
| 6,151,746 | A | 11/2000 | Lewis, Jr. ..................... 15/187 | 2004/0060137 A1 | 4/2004 | Eliav ........................... 15/22.1 |
| 6,168,434 | B1 | 1/2001 | Bohm-Van Diggelen .... 433/141 | 2004/0154112 A1 | 8/2004 | Braun et al. .................. 15/22.1 |
| 6,182,323 | B1 | 2/2001 | Bahten ................... 15/230.16 | 2004/0200016 A1 | 10/2004 | Chan et al. .................... 15/22.1 |
| 6,182,365 | B1 | 2/2001 | Tseng et al. ................. 30/34.2 | 2005/0000048 A1 | 1/2005 | Hohlbein ..................... 15/110 |
| 6,190,367 | B1 | 2/2001 | Hall ............................ 604/290 | 2005/0015901 A1 | 1/2005 | Gavney |
| 6,219,874 | B1 | 4/2001 | van Gelder et al. ........ 15/167.1 | 2005/0015907 A1 | 1/2005 | Georgi et al. ............... 15/167.1 |
| 6,240,590 | B1 | 6/2001 | Nesbit ....................... 15/210.1 | 2005/0049155 A1 | 3/2005 | Gavney, Jr. et al. ......... 510/108 |
| 6,245,032 | B1 | 6/2001 | Sauer et al. .................. 601/162 | 2005/0060822 A1 | 3/2005 | Chenvainu et al. ............. 15/28 |
| 6,254,390 | B1 | 7/2001 | Wagner ....................... 433/216 | 2005/0102780 A1 | 5/2005 | Hohlbein ..................... 15/110 |
| 6,272,713 | B1 | 8/2001 | Lotwin ................. 15/104.061 | 2005/0102783 A1 | 5/2005 | Hohlbein ................... 15/167.1 |
| 6,276,021 | B1 | 8/2001 | Hohlbein ................... 15/167.1 | 2005/0166342 A1 | 8/2005 | Hohlbein ..................... 15/110 |
| 6,299,508 | B1 | 10/2001 | Gagliardi et al. .............. 451/28 | | | |
| 6,311,358 | B1 | 11/2001 | Soetewey et al. ............. 15/110 | | | |
| 6,311,360 | B1 | 11/2001 | Lanvers ..................... 15/191.1 | | | |
| 6,314,605 | B1 | 11/2001 | Solanki et al. ............. 15/167.1 | | | |
| 6,319,332 | B1 | 11/2001 | Gavney, Jr. et al. ............. 134/6 | | | |
| 6,349,442 | B1 | 2/2002 | Cohen et al. ................. 15/22.1 | | | |
| 6,421,867 | B1 | 7/2002 | Weihrauch ..................... 15/28 | | | |
| 6,446,295 | B1 * | 9/2002 | Calabrese ...................... 15/28 | | | |
| 6,463,619 | B2 | 10/2002 | Gavney, Jr. ................... 15/117 | | | |
| 6,510,575 | B2 | 1/2003 | Calabrese ................... 15/22.1 | | | |
| 6,513,182 | B1 | 2/2003 | Calabrese et al. ............. 15/110 | | | |
| 6,553,604 | B1 | 4/2003 | Braun et al. ............... 15/167.1 | | | |
| 6,571,417 | B1 | 6/2003 | Gavney, Jr. et al. ........... 15/117 | | | |
| 6,599,048 | B2 | 7/2003 | Kuo ............................ 401/269 | | | |
| 6,643,886 | B2 | 11/2003 | Moskovich et al. ........ 15/167.1 | | | |
| 6,647,585 | B1 | 11/2003 | Robinson ...................... 15/322 | | | |
| D483,184 | S | 12/2003 | Geiberger et al. ............. D4/104 | | | |
| 6,658,688 | B2 | 12/2003 | Gavney, Jr. ................... 15/117 | | | |
| 6,658,692 | B2 | 12/2003 | Lenkiewicz et al. ........... 15/320 | | | |
| 6,668,418 | B2 | 12/2003 | Bastien ........................ 15/245 | | | |
| 6,725,493 | B2 | 4/2004 | Calabrese et al. ............. 15/110 | | | |
| 6,751,823 | B2 | 6/2004 | Biro et al. .................... 15/22.1 | | | |
| 6,813,793 | B2 | 11/2004 | Eliav ........................... 15/22.2 | | | |
| 6,817,054 | B2 | 11/2004 | Moskovich et al. ........ 15/167.1 | | | |
| 6,820,299 | B2 | 11/2004 | Gavney, Jr. ................... 15/117 | | | |
| 6,820,300 | B2 | 11/2004 | Gavney, Jr. ................... 15/117 | | | |
| 6,859,969 | B2 | 3/2005 | Gavney, Jr. ................... 15/117 | | | |
| 6,865,767 | B1 | 3/2005 | Gavney, Jr. ................... 15/114 | | | |
| 6,886,207 | B1 | 5/2005 | Solanki ....................... 15/110 | | | |

FOREIGN PATENT DOCUMENTS

| | | |
|---|---|---|
| GB | 2 040 161 A | 8/1980 |
| GB | 2 214 420 A | 9/1989 |
| GB | 2 319 170 A | 5/1998 |
| GB | 2 371 217 A | 7/2002 |
| JP | 9-140456 | 3/1997 |
| WO | WO 96/15696 | 5/1996 |
| WO | WO 96/20654 | 7/1996 |
| WO | WO 96/28994 | 9/1996 |
| WO | WO 97/16995 | 5/1997 |
| WO | WO 98/18364 | 5/1998 |
| WO | WO 98/22000 | 5/1998 |
| WO | WO 99/37181 | 7/1999 |
| WO | WO 00/64307 | 8/2000 |
| WO | WO 00/49911 | 11/2000 |
| WO | WO 00/76369 A2 | 12/2000 |
| WO | WO 01/01817 A1 | 1/2001 |
| WO | WO 01/21036 A1 | 3/2001 |
| WO | WO 03/030680 A1 | 4/2003 |
| WO | WO 03/043459 A2 | 5/2003 |
| WO | WO 2004/041023 A2 | 5/2004 |
| WO | WO 2004/064573 A1 | 8/2004 |

OTHER PUBLICATIONS

The Gillette Company, 2004 Annual Report and 2005 Proxy Statement.

* cited by examiner

ORAL-CARE DEVICE AND SYSTEM

RELATED APPLICATIONS

This application is a Continuation-in-Part of application Ser. No. 10/839,988, titled "DENTITION CLEANING DEVICE AND SYSTEM, filed May 5, 2004, now U.S. Pat. No. 6,944,903 which is a Continuation Application of the application Ser. No. 10/382,559, titled "DENTITION CLEANING DEVICE AND SYSTEM", filed Mar. 5, 2003, now U.S. Pat. No. 6,820,299 which is a Continuation Application of the application Ser. No. 09/588,686, titled "DENTITION CLEANING DEVICE AND SYSTEM", filed Jun. 5, 2000, and now U.S. Pat. No. 6,571,417, which is a Continuation-in-part of application Ser. No. 09/330,704 entitled "SQUEEGEE CLEANING DEVICE AND SYSTEM" filed Jun. 11, 1999 and now U.S. Pat. No. 6,319,332. The application Ser. No. 10/839,988, titled "DENTITION CLEANING DEVICE AND SYSTEM, filed May 5, 2004, the application Ser. No. 10/382,559, titled "DENTITION CLEANING DEVICE AND SYSTEM", filed Mar. 5, 2003, the U.S. Pat. No. 6,319,332 and the U.S. Pat. No. 6,571,417 are all hereby incorporated by reference.

FIELD OF THE INVENTION

This invention relates generally to oral-care devices and systems. More specifically, this invention relates to oral care devices and systems that irrigate and brush and/or wipe teeth and gums.

BACKGROUND

Treating surfaces is an activity that occupies a considerable portion of most peoples time. For example, household surfaces are regularly cleaned and polished and/or require the application of treatment or cleaning materials to the household surfaces. Also, many industrial processes, such as cleaning floors and polishing wafers, require contacting surfaces to clean the surfaces and/or apply materials to the surfaces. Likewise, there are a number of medical and/or personal hygiene activities that require treating surfaces with contact elements to treat or clean the surfaces. A particular example is oral-care, which requires very specialized treatment of a surface in cleaning teeth and gums.

There are a number of different systems and devices available for cleaning teeth and gums. A number of these available systems and devices are inefficient at cleaning teeth and gums and require multiple pass scrubbing with oral cleaning agents, such as tooth pastes or gels, to effectively clean the teeth and gums. Typically, toothbrushes, for example, do not efficiently apply the oral cleaning agents to the teeth and gums and can be abrasive, causing loss of healthy gum tissue and/or damage to teeth. Further, toothbrushes can require a high degree of technique and/or dexterity to be used effectively for cleaning teeth and gums.

What is needed is a dentition cleaning system and device that can efficiently apply oral cleaning agents to teeth and gums and that can clean teeth and gums without a high degree of technique or dexterity. Further, what is needed is a dentition cleaning system and device that is less abrasive to teeth and gums than a conventional bristle toothbrush.

SUMMARY OF THE INVENTION

The present invention is directed to a device comprising a head that is configured to clean surfaces, treat surfaces and/or apply materials to surfaces. Preferably, the head is a cleaning head is configured to clean and/or treat teeth and gums. However, it will be clear to one skilled in the art that the present invention can equally be applied to devices that are configured to clean any number of different surfaces including, but not limited to, floors, cars, wafers and/or appliances.

In accordance with the embodiment of the present invention an oral-care system includes a cleaning head with a region that is configured to move. The region can be configured to vibrate, rotate, oscillate or otherwise automatically move. The region includes bristle tufts, nodules, one or more squeegees or any combination thereof. The cleaning head also includes one or more apertures to dispense an oral-care liquid, such a water, liquid toothpaste, mouthwash and the like, to teeth and gums while brushing the teeth and gums with the cleaning head. The one or more apertures can be located on the region configured to move, on a separate portion of the cleaning head that is stationary, configured to move independently or a combination thereof, such as described in detail below.

The oral care system preferably includes a power handle or motorized handle, hereafter handle, that is configured to power and move a region of the cleaning head. The cleaning head is preferably configured to detachably couple to the handle. The handle can include an internal battery source that is disposable or rechargeable. In addition to, or alternatively to, the battery source, the oral care system can include or be configured to couple to an external power source. The handle also preferably includes switch or control means that can selectively power the cleaning head and control pulse rates or flow rates of the oral-care liquid through the one or more apertures.

The oral-care system includes a liquid delivery means or irrigation means, which includes a pump mechanism, fluid source and one or more feed line. The pump mechanism is preferably configured to deliver bursts of the oral-care liquid through the one or more apertures, also referred to herein as liquid pulses. The fluid source is configured to hold the oral-care fluid and is coupled to the cleaning head through the one or more feed lines for delivering the oral-care liquid to the cleaning head via the pump mechanism. The pump mechanism and/or the fluid source can be internal to the handle or external and separate from the handle. For example, the pump mechanism and/or the fluid source can be integrated into caddy structure or stand section for docking and for storing the handle portion of the oral-care system. Where the fluid source is internal to the handle, the handle can removable containers or cartridges of pre-filled oral-care solution configured fit into a compartment of the handle.

In accordance with further embodiments of the invention, the oral-care system includes a first fluid source for supplying a first oral-care fluid and a second fluid for supplying a second oral care fluid. In accordance with the embodiments of the invention the first oral-care fluid source is internal to the handle and the second oral-care fluid source is external to the handle. In use the pump mechanism can be configured to deliver the first oral-care liquid and the second oral-care liquid at controlled or selectable rates. The pump mechanism can also be configured to mix the first oral care fluid and the second oral care fluid and deliver a mixture of the first and second oral-care cleaning fluids to the cleaning head. Alternatively, the oral-care system can be configured to have separate feed lines and apertures for delivering the first and second oral care solutions to the cleaning head.

In accordance with the present invention, a device comprises a cleaning head with two or more regions, wherein at least one of the regions preferably comprises a squeegee element configured to treat a working surface and at least one of the regions comprises bristles. In accordance with a preferred embodiment of the invention, at least one of the regions is configured to move independently of another of the regions. To move independently, herein, means that one of the regions is stationary while another region moves or that the regions move separately from one or more of the other, but does not necessarily mean that the regions are not synchronized to move with a similar or the same motion or that the regions are not coupled to the same mechanism to drive the motion of the regions. Preferably, one or more of the regions are configured to vibrate, rotate, oscillate or otherwise automatically move relative to and independently from another of the regions. In accordance with further embodiments of the invention two or more of the regions comprises bristle and squeegee elements. In still further embodiments of the invention, one or more of the regions of the cleaning head comprises nodules, i.e., resilient protrusions with any number of different geometries such as described below and further described in U.S. Pat. No. 6,865,767, filed Sep. 19, 2001, and titled "DEVICE WITH MULTI-STRUCTURAL CONTACT ELEMENTS," the contents of which are hereby incorporated by reference.

The squeegee elements utilized in the present invention can have any number of different geometries including curved, rounded angled, corrugated, pointed and/or textured walls and/or wiping edges. Squeegee elements can include squeegee segments with one or more terminus ends and/or squeegee segments that form matrices of squeegee compartments and continuous squeegee segments that encircle portions of regions. Squeegees utilized in the present invention can be formed from any number of different materials, but are preferably formed from a resilient polymeric material such as silicon, latex, rubber, polyurethane or a combination thereof. Preferably, squeegees, or a portion thereof, are formed from a material, or materials, that can be molded and that result in squeegee elements with hardness values in a range of 10 to 100 Shores A, as defined in the D2240-00 Standard Test Method for Rubber Property-Durometer Hardness, published by the American Society for Testing Materials, the contents of which are hereby incorporated by reference. Additional details of squeegee configurations are provided in the U.S. Pat. No. 6,319,332, titled "SQUEEGEE DEVICE AND SYSTEM," and U.S. Pat. No. 6,571,417, titled "DENTITION CLEANING DEVICE AND SYSTEM," the contents of which are also both hereby incorporated by reference.

Squeegees, in accordance with still further embodiments of the present invention, include an abrasive material that is integrated with the material(s) used to form the squeegees and/or are applied to surfaces of squeegee walls and/or edges after they are formed. Methods and materials for making molded abrasive structures are described in U.S. Pat. No. 6,126,533, and titled "MOLDED ABRASIVE BRUSH", the contents of which are hereby incorporated by reference.

In accordance with a preferred embodiment of the invention, a squeegee element comprises an elongated squeegee segments with smaller fins that protrude from walls of the elongated squeegee segment and provide top wiping edges and side wiping edges, such as described in detail in U.S. Pat. No. 6,859,969, filed Jun. 3, 2003, entitled "MULTI-DIRECTIONAL WIPING ELEMENTS AND DEVICES USING THE SAME", the contents of which are hereby incorporated by reference.

In accordance with a further embodiment of the present invention, a first region comprising bristles, squeegee elements and/or nodules encircles a second region comprising bristles, squeegee elements and/or nodules, wherein one or both of the first region and the second region are configured to move. For example, the first region is configured to rotate or oscillate relative to the second region and/or the second region is configured to rotate or oscillate in an opposite direction at the same or at a faster rate.

For clarity, devices have been described below with a first region and a second region. However, it will be clear to one skilled in the art, that systems and devices of the present invention can be configured with any number of regions each with contact elements (e.g., squeegees, bristles and nodules), wherein one or more of the regions are configured to move independently from one or more of the other regions. Devices, in accordance with further embodiment of the invention, are configured with apertures to dispense materials onto a working surface and/or remove materials from the working surface, such as those described in U.S. Pat. Nos. 6,319,332 and 6,571,417, referenced previously.

DETAILED DESCRIPTION

Figure 1A:
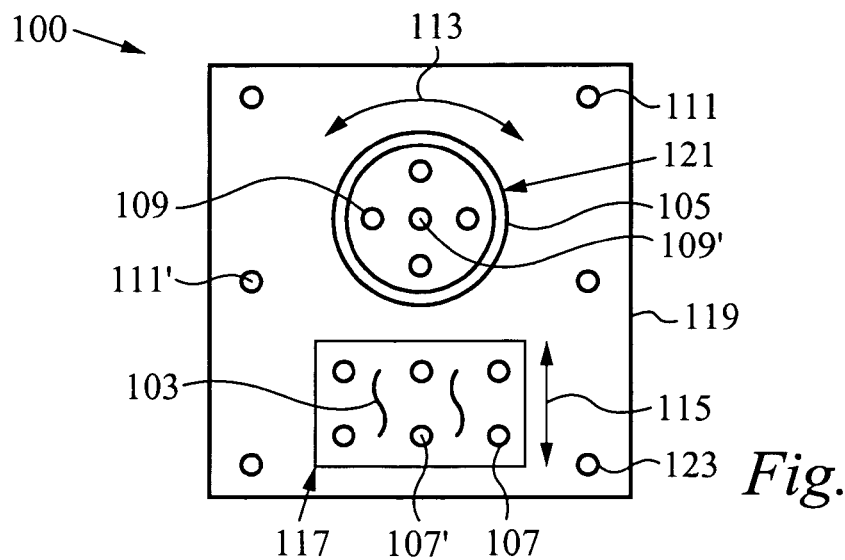
FIGS. 1A-C show cleaning heads with independently movable regions, in accordance with the embodiments of the invention.

FIG. 1A shows a schematic top view of a cleaning head configuration 100, in accordance with the embodiments of the invention. The cleaning head configuration 100 comprises a first region 121 and a second region 117 that are configured to move independently from each other. In accordance with the embodiments of the invention, the first region 121 comprises a continuous squeegee element 105 that encircles a portion of the first region 121, bristles, bristle tufts and/or nodules 109 protruding therefrom. The first region 121 can also include one or more apertures 109' for dispensing an oral-care liquid from the cleaning head, such as described in detail below.

Figure 1B:
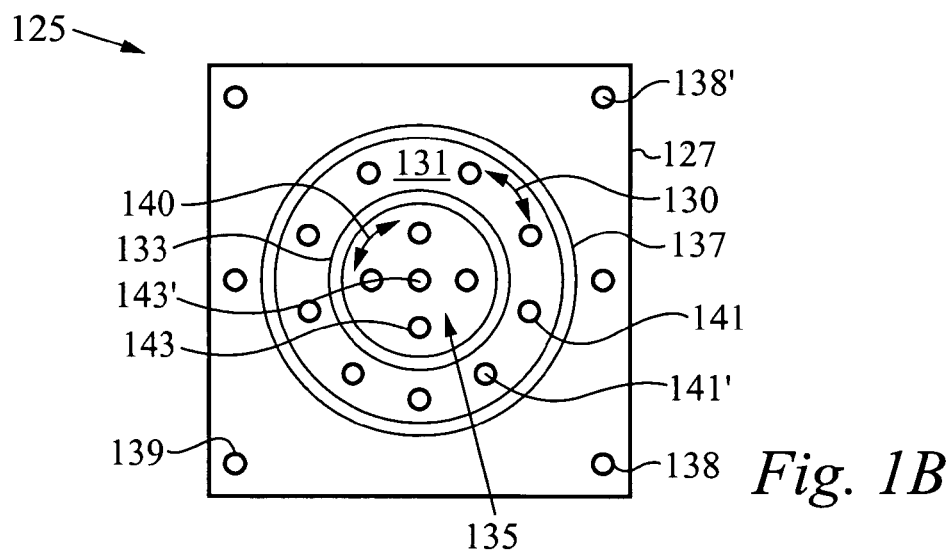
Figure 1C:
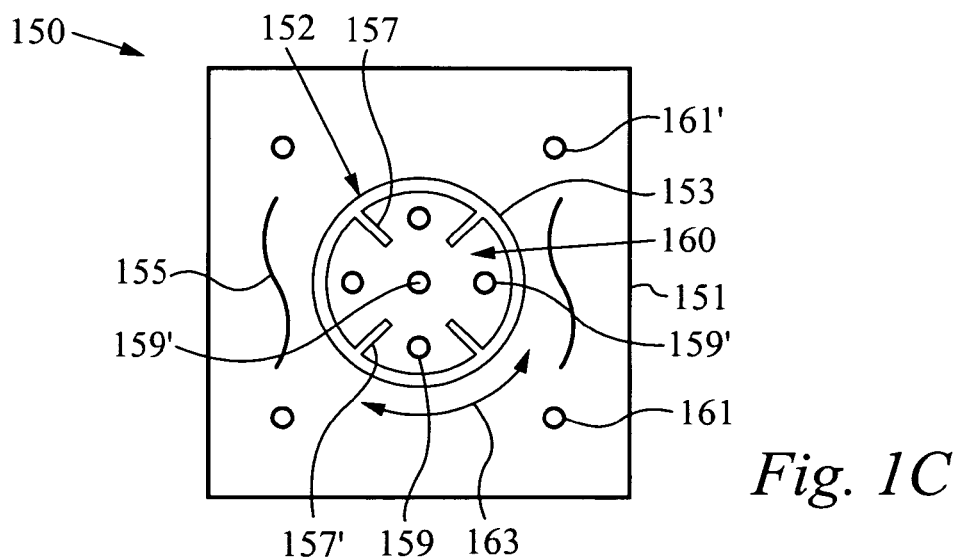

While FIGS. 1A-C are described as having bristles or bristle tuft, it will be clear to one skilled in the art and from the description below that the cleaning head configuration can include, in place of bristle or bristle tufts or in addition to bristles or bristle tufts, nodules such as those described with reference to FIGS. 6A-H and FIGS. 7A-G below.

Still referring to FIG. 1A, the first region 121 is preferably configured to rotate and/or oscillate, as indicated by the arrow 113, independently from the second region 117, which can be stationary or configured to move, for example in a backward and forward motion as indicated by the arrow 115. The second region 117 preferably comprises bristle, bristle tufts and/or nodules 107 that protrude therefrom and can also include one or more curved squeegee elements or wave-shaped squeegee elements 103. The cleaning head configuration 100 includes a support structure 119 with bristle, bristle tufts and/or nodules 111 and 123 protruding therefrom. Preferably the aperture 109' is configured to dispense an oral-care liquid from the clearing head 100 while at least one of the first region 121 and the second region 117 are moving.

FIG. 1B, shows a schematic top view of a cleaning head configuration 125, in accordance with further embodiments of the invention. The cleaning head configuration 125 comprises a first region 131 and a second region 135 that are configured to move independently from each other. In accordance with this embodiment, the first region 131 comprises a first continuous squeegee 137 that encircles a first set of bristles and/or nodules 141 protruding from the first region 131 and encircles the second region 135. The first region 131 can include one or more apertures 141' for dispensing an oral-care solution. The second region 135 comprises a second continuous squeegee 133 the encircles a second set of bristles and/or nodules 143 protruding from the second region 135 and at least one aperture 143, such as described above. Accordingly, first region 131 can be described as surrounding the second region 135. The second region second region 135 can also include one or more apertures 143' for dispensing an oral-care solution. Preferably the at least one aperture 143' is configured to dispense the oral-care liquid from the clearing head 125 while at least one of the first region 131 and the second region 117 are moving.

Still referring to FIG. 1B, the first region 131 and the second region 135 are preferably configured to rotate and/or oscillate as indicated by the arrows 130 and 140, respectively. In accordance with a preferred embodiment of the invention, the first region 131 and the second region 135 are configured to move in opposite directions while rotating and/or oscillating while an oral-care liquid is dispensed through the aperture 143. It will be clear to one skilled in the art that the first region 131 and the second region 135 can be configured to move in the same direction at the same or at a different rate of rotation and/or oscillation. In accordance the invention, the cleaning head configuration 125 can also have support structure 127 with bristle, bristle tufts and/or nodules 138 and 139 protruding therefrom.

FIG. 1C, shows a schematic top view of a cleaning head configuration 150 in accordance with yet further embodiments of the invention. The cleaning head configuration 150 comprises at least one region 160 that is configured to rotate, oscillate and/or otherwise move in one or more directions, as indicated by the arrow 163. The region 160 preferably includes one or more squeegee elements 152. In accordance with the embodiments of the invention, the squeegee element 152 comprises a primary squeegee segment 153 with squeegee wiping fins 157 and 157' that protrude from an inner wall of the primary squeegee segment 153.

Still referring to FIG. 1C, the primary squeegee segment 153, in accordance the embodiments of the invention, is a continuous segment 153 that encircles at least a portion of the region 160, bristles, bristle tufts and/or nodules 159 protruding from the encircled portion of the region 160 and at least on aperture 159' for dispensing an oral-care liquid from the cleaning head. Preferably, the at least one aperture 159' is configured to dispense the oral-care liquid from the clearing head 150 while the squeegee element 152 is moving as indicated by the arrow 163. While the squeegee wiping fins 157 and 157' are shown here as protruding from an inner wall of the continuous primary squeegee segment 153, it will be clear to one skilled in the art that in addition to the squeegee wiping fins 157 and 157' or alternatively to the squeegee wiping fins 157 and 157', the squeegee element 152 can include one or more squeegee wiping fins protruding from an outer wall of the continuous squeegee segment 153. Also, while the primary squeegee segment 153 is shown here as a continuous squeegee segment, any number of geometries are contemplated, such as those described with reference to FIGS. 4A-M below. Squeegee configurations can have squeegee wiping fins with contoured or shaped wiping edges and/or wiping walls. Also, squeegee wiping fins can have wiping edges that protrude to the same or different heights than the wiping edges of a primary squeegee segment to which they are attached. A number of squeegee element configurations that have squeegee wiping fins are described in U.S. Pat. No. 6,859,969, filed Jun. 3, 2003, and titled "MULTI-DIRECTIONAL WIPING ELEMENTS AND DEVICES USING THE SAME," referenced previously.

FIG. 2 shows an electric powered oral-care system 200, in accordance with the embodiments of the invention. The oral-care system 200 includes a power handle or motorized handle 201, hereafter handle, that is configured to power and move one or more regions 233 and 239 of a cleaning head 231. The handle includes a motor 226 and any suitable drive mechanism for transferring motion to the first 233 and second region of the cleaning head 231.

The cleaning head 231 is preferably configured to detachably couple to the handle 201 through and attachment means 228. The attachment means can be any attachment means know in the art, including a twist and lock mechanism, which can securely fasten the cleaning head 231 to the handle 201. The handle 210 can include an internal battery source 223 that is disposable or rechargeable. In addition to, or alternatively to, the battery source 223, the oral-care system 200 can include, or can be configured to couple to, an external power source (not shown). The handle 201 also preferably includes switch 224 with controls 225 and 225 for selectively powering the cleaning head 231 and controlling a pulse rate, or flow rate of an oral-care liquid through the one or more apertures 202 on the cleaning head 231. Preferably, the oral-car system 200 can deliver the oral-care liquid to the cleaning head 231 both when the regions 233 and 239 are moving and when both the region 233 and 239 are stationary. Preferably, the oral-care apparatus 200 includes a timer, such that the cleaning head and/or the irrigation system can be energizing with the controls 225 and 225 for preferred amounts of time to clean and/or irrigate teeth and gums with the oral-care apparatus 200.

The cleaning head 231 preferably includes a first region 233 that is configured to rotate or oscillate and a second region 251 that is configured move back and forth or vibrate. The first region 233 preferably includes a continuous squeegee or prophy-cup like structure 233 that substantially encircles the aperture 202 which helps to control "spray-off" of the oral-care liquid as the oral-care liquid is sprayed, pulsed or otherwise delivered to teeth and gum through the cleaning head 231. The prophy-cup like structure 233, while shown as a solid continuous cup can also be formed from curved closely spaced squeegee segments arranged in a circular pattern or curved and/or linear squeegee segments that are closely spaced or overlap in a flower pedal-like arrangement. The second region 251 preferably includes bristles, but can include bristles, squeegees, nodules and any combination thereof.

Figure 2A:
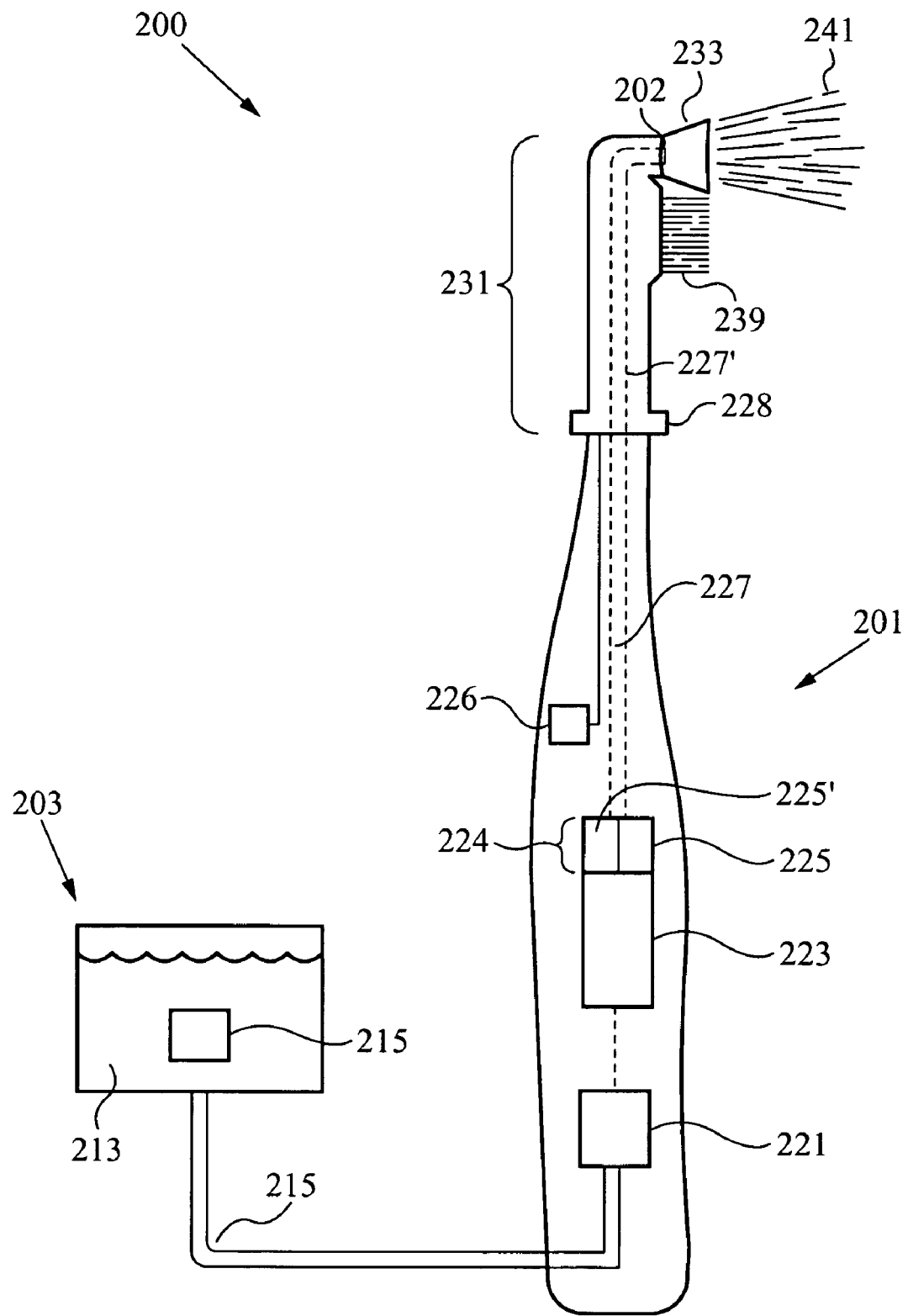
FIG. 2A shows an electric powered oral-care device comprising a power cleaning head an irrigation mechanism, in accordance with the embodiments of the invention

Still referring to FIG. 2A, the oral care system 200 includes a liquid delivery means or irrigation means, which can include and pump mechanism 221, fluid source 203 and one or more internal feed lines 227 and 227'. The pump mechanism 221 is preferably configured to deliver bursts, also referred to as pulses, of the oral-care liquid 213 through the one or more apertures 202 of the cleaning head 231. The fluid source 203 is configured to hold the oral-care fluid 203 and is coupled to the handle 201 through one or more external feed lines 215 for delivering the oral-care liquid to the cleaning head via the pump mechanism. In addition to the pump mechanism 221, or alternatively to the pump mechanism 221, the fluid source 203 can also include a pump 215 for urging the oral-care fluid into the handle 201 and/or delivering the oral-care fluid through the aperture 202 of the cleaning head 231.

In accordance with further embodiments of the invention, the oral-care system 200 includes a fluid source that is internal to the handle. The fluid source can be held in removable containers or cartridges that are pre-filled with an oral-care liquid that fit into a compartment of the handle 201 and interface with the pump mechanism 221, such that the oral-care liquid is pumped from the removable container or cartridge to the cleaning head 231.

In accordance with yet further embodiments of the invention, the oral-care system 200 includes a first fluid source for supplying a first oral-care fluid and a second fluid for supplying a second oral care fluid. The first oral-care fluid source is internal to the handle and the second oral-care fluid source is external to the handle. In use the pump mechanism can be configured to deliver the first oral-care liquid and second oral-care liquid at controlled or selectable rates. The pump mechanism can also be configured to mix the first oral care fluid and the second oral care fluid and deliver a mixture of the first and second oral-care cleaning fluids to the cleaning head. Alternatively, the oral-car system can be configured to have separate feed lines and apertures for delivering the first and second oral care solutions to the cleaning head 231. The first fluid source can be configured to hold powderers, tables or other solids that are mixed with fluid form the second fluid supply source to form an add-mixture oral-care fluid that is then delivered to and dispensed from the cleaning head 231.

In accordance with the embodiments of the invention, the electric powered oral-care apparatus 200 comprises a power or recharging station for docking the handle 201. The power or recharging station comprises means for plugging the power or recharging station into an electrical receptacle and recharging the battery 223 of the oral-care apparatus 200, wherein the battery 223 is configured for providing power to a driver mechanism 226 that moves one or both of the regions 233 and 239. Alternatively, or in addition to the power supply mechanism described above, the apparatus 200 can be configured to be powered with disposable batteries that are housed in the handle 201.

Figure 2B:
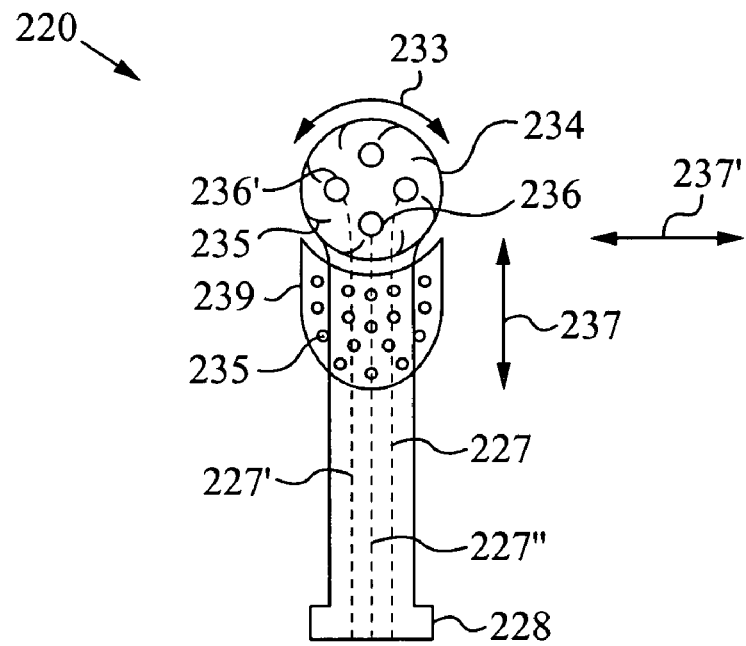
FIG. 2B-C show power head configurations, in accordance with the embodiments of the invention.

FIGS. 2A-B show oral-care cleaning heads 220 and 240 that are configured to detachably couple to a power handle 201, such as described with reference to FIG. 2A. Referring to FIG. 2B, the oral-care cleaning head 220 comprising a first region with a prophy-cup structure 234 with fins 235. The prophy-cup structure 234 is configured to rotate or oscillate, as indicated by the arrow 233. The prophy-cup structure 234 surrounds, cups or encircles a plurality of apertures 236 and 236' for dispensing an oral-care solution. The oral-care cleaning head 220 includes an attachment means 228 for detachably securing the oral-care cleaning head 220 to the handle 201, such as described above. The oral-care cleaning head 220 also includes any suitable number of feed lines 227, 227, and 227" required for delivering the oral-care solution to the apertures 236 and 236'. The oral-care cleaning head 220, also includes a second region 239 that includes bristles 235. The second region 239 is configured to move up and down, as indicated the arrow 233, back and forth, as indicated by the arrow 237' or vibrate in any number of directions.

Figure 2C:
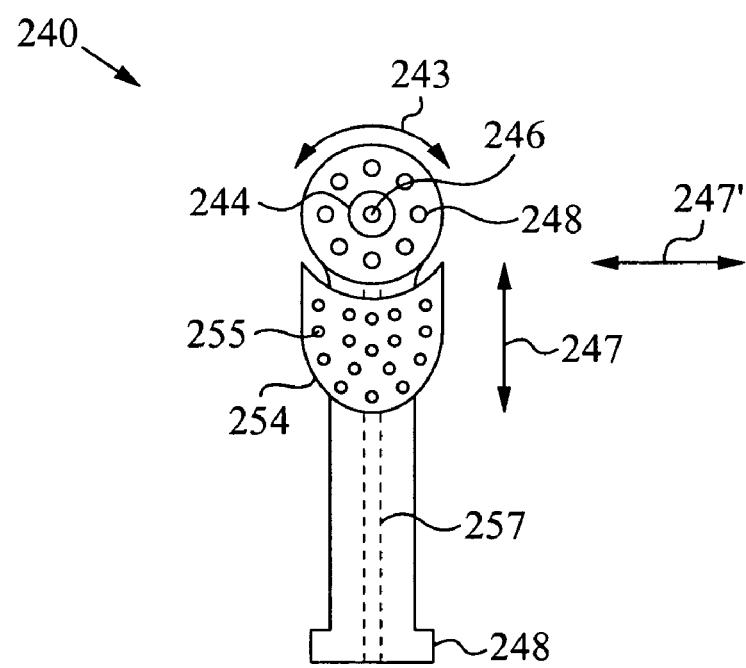

Referring to FIG. 2C, the oral-care cleaning head 240 comprising a first region with a prophy-cup structure 244 configured to rotate or oscillate, as indicated by the arrow 243. The prophy-cup structure 244 surrounds, cups or encircles an aperture 246' for dispensing an oral-care solution. The prophy-cup structure 244 is surrounded or encircled by groups of bristles and/or nodules 248 that protrude from the first region and are preferably configured to rotate or oscillate simultaneously with the prophy-cup structure, as indicated by the arrow 243. The oral-care cleaning head 240 includes and attachment means 248 for detachably securing the oral-care cleaning head 240 to the handle 201, such as described above. The oral-care cleaning head 240 also includes a feed line 257 for delivering the oral-care solution to the aperture 246. The oral-care cleaning head 240, also includes a second region 254 that includes bristles 255. The second region 239 is configured to move up and down, as indicated the arrow 247, back and forth, as indicated by the arrow 247' or vibrate in any number of directions.

Figure 3A:
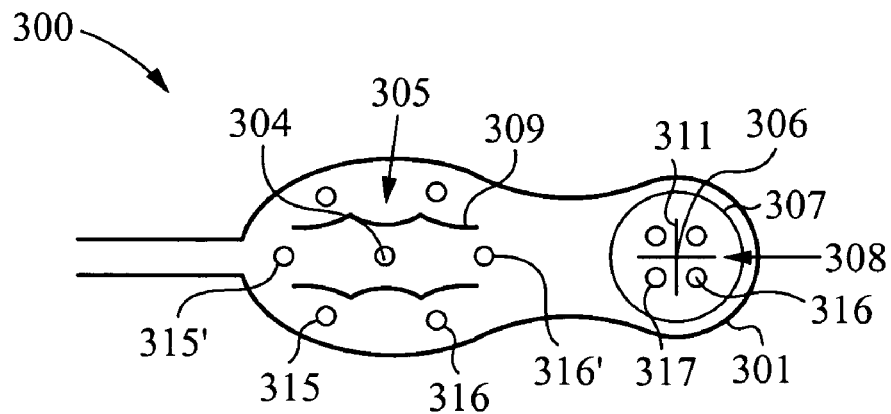
FIGS. 3A-C show oral-care cleaning heads with movable regions comprising squeegee elements, bristles and/or nodules in accordance with the embodiments of the invention.
Figure 3B:
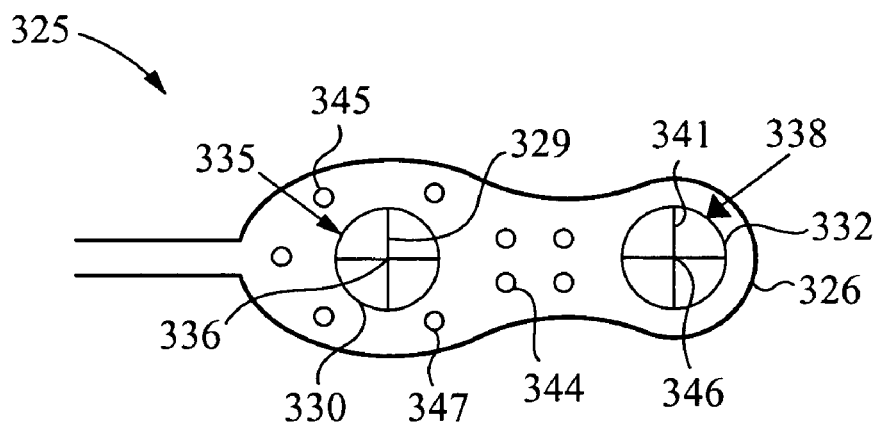
Figure 3C:
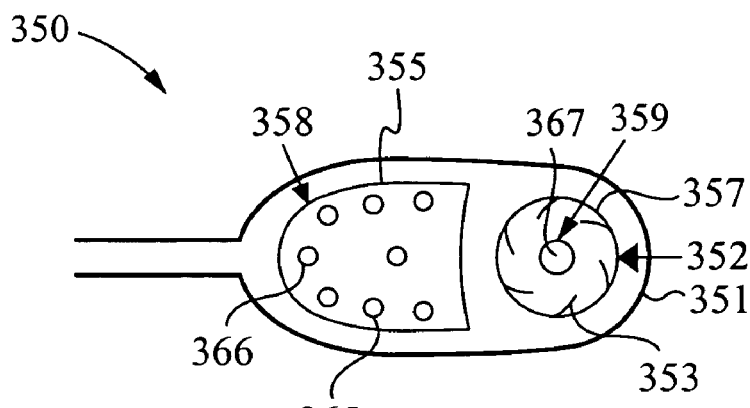

FIGS. 3A-C show oral-care cleaning heads 300, 325 and 350 with movable regions comprising squeegee elements, bristles, nodules and/or combinations thereof and apertures for dispensing an oral-care solution, such as described above. Referring now to FIG. 3A, the oral-care cleaning head 300 comprises a base structure 301 for supporting a first region 305 and a second region 307. The first region 305 comprises one or more squeegee elements 309 protruding therefrom. The squeegee elements 309 are shown here as wave-like, wherein the squeegee elements 309 have curved squeegee walls that extend in a number of directions two or more times (i.e., wave-like). While the squeegee elements 309 are shown with curved or wave-like walls, squeegee elements with linear or straight squeegee walls are also contemplated. Also, as described above walls of the squeegee elements and/or the top wiping squeegee edges of the squeegee elements 309 can be contoured or shaped in any number of different ways. In addition to the squeegee elements 309, the first region 305 can also have one or more tufts of bristles 315 and 315' and/or nodules 316 and 316' protruding therefrom in directions that are the same or different from that of the squeegee element 309. The first region 305 also preferably includes one or more apertures 304 for dispensing an oral-care solution.

Still referring to FIG. 3A, the second region 308 of the oral-care cleaning head 300 can comprise a squeegee element 311 protruding therefrom. The squeegee element 311 can have any number of different geometries, but is shown here as a cross-shaped squeegee element 311, with a number of squeegee segments intersecting at a common position 306. The second region 308 of the oral-care cleaning head 300 can also comprise bristle tufts 317 and/or nodules protruding therefrom in directions that are the same or different from that of the squeegee element 311. The second region can also includes an apertures 316 for dispensing an oral-care solution, such as described above. Also, the second region 308 of the oral cleaning head 300 can comprise a continuous squeegee element 307 encircling a portion of the second region 308. In operation, the second region 308 rotates, oscillates, vibrates and/or otherwise moves relative to the first region while the oral-care liquid is dispensed from one or more of the apertures 304 and 316 for cleaning teeth and/or gums.

Referring now to FIG. 3B, the oral-care cleaning head 325 comprises a base structure 326 for supporting a first region 335 and a second region 338. The first region 335 comprises a first squeegee element protruding therefrom. The first squeegee element is shown here having a cross-shaped squeegee segment 329 with a number of squeegee segments intersecting at a common position 336. Also, the first squeegee element can comprise a continuous squeegee wall segment 330 encircling a portion of the first region 335 and the cross-shaped squeegee segment 329, wherein the walls of the cross-shaped squeegee segment 329 intersect with the continuous squeegee wall segment 330 and wherein the first squeegee element is capable of cupping and holding an oral-care solution, paste and/or gel during a cleaning operation. Also, it is noted that the first region 335 can include one or more bristle tufts and/or nodules (not shown) protruding therefrom in directions that are the same or different from that of the first squeegee element.

Still referring to FIG. 3B, the oral-care cleaning head 325 comprises a second region 338 with a second squeegee element protruding therefrom. The second squeegee element is shown here having a cross-shaped squeegee segment 341 with a number squeegee segments intersecting at a common position 346 and a continuous squeegee wall segment 332 encircling a portion of the second region 338 and the cross-shaped squeegee segment 341. In accordance with the embodiments of the invention, the second region 338 can also include one or more bristle tufts and/or nodules (not shown) protruding therefrom and/or the oral-care cleaning head 325 can have one or more bristle tufts 345 protruding and/or nodules 347 protruding from the support structure 326 in directions that are the same or different from that of the first or second squeegee element. Preferably, the oral-care cleaning head 325 also include one or more apertures 344 on the support structure 326 for dispensing an oral-care solution, while the first region 335 and the second region 338 rotate, oscillate, vibrate and/or otherwise move independently of each other. For example, the first region 335 can rotate or oscillate in one direction while the second region 338 can rotate or oscillate in an opposite direction. While the first squeegee element and the second squeegee element are shown here as combinations of cross-shaped segments 329 and 341 and surrounding continuous squeegee segments 330 and 332, respectively, any number of squeegee element geometries and shapes are contemplated including, but not limited to, those described with reference to FIGS. 4A-M.

Referring now to FIG. 3C, the oral-care cleaning head 350 comprises a support structure 351 for supporting a first region 358 and a second region 359. The first region 358 comprises bristles 365 and/or nodules 366 protruding therefrom. The second region 359 comprises a squeegee element 352. The squeegee element 352 preferably comprises a continuous squeegee wall segment 357 that encircles a portion of the second region 359 and squeegee fins 353. The squeegee fins 353 protrude from an inner wall of the continuous squeegee wall segment 357. The squeegee fins 353 can protrude from the continuous squeegee wall segment 357 at any angle suitable for the application at hand and can protrude to the same or a different height from the support structure 351 than the top wiping edges of the continuous squeegee wall segment 357. Squeegee elements with squeegee fins are further described in U.S. Pat. No. 6,859,969, referenced previously. Preferably, the second region 359 also includes an aperture 367 that is surrounded by the squeegee element for dispensing an oral-care solution.

In operation, the second region 359 rotates, oscillates, vibrates and/or otherwise moves independently of the first region 358 while the oral-care solution is dispensed from the aperture 367 for cleaning teeth and gums. For example, the second region 359 can rotate or oscillate while the first region 358 moves in a back and forth motion and/or vibrates, such as described above with reference to FIGS. 1A-C.

Still referring to FIG. 3C, the oral-care cleaning head 350 can also include a continuous squeegee element 355 that surrounds a portion of the first region 358. Preferably, the second region 359 of the oral cleaning head 350 further comprises one or more bristle tufts or nodules 367 that are surrounded by the continuous squeegee wall segment 357 and that are configured to move along with the squeegee element 352. While the oral-care cleaning heads 300, 325 and 350 have been described as having squeegee elements, bristle, nodules and combinations thereof, it will be clear to one skilled in the art that bristles are not required.

FIGS. 4A-M illustrate top views of squeegee configurations, or portions thereof, in accordance with further embodiments of the invention, wherein intersecting squeegee segments have different lengths, the same lengths, different heights or the same heights to provide top wiping edges and side wiping edges. Squeegee configurations, or portions thereof, as described with reference to FIGS. 4A-M, can include bristles and/or nodules that protrude from a support surface to the same height or different heights as the squeegee wiping edges of the squeegee segments. Also, the squeegee configurations can include bristles and/or nodules that protrude from the support surface at the same angles or different angles from that of the squeegee segments relative to the support surface. Preferably, the squeegee configuration includes one or more apertures on the support structure for dispensing an oral-care solution, such as described in detail above.

Figure 4A:
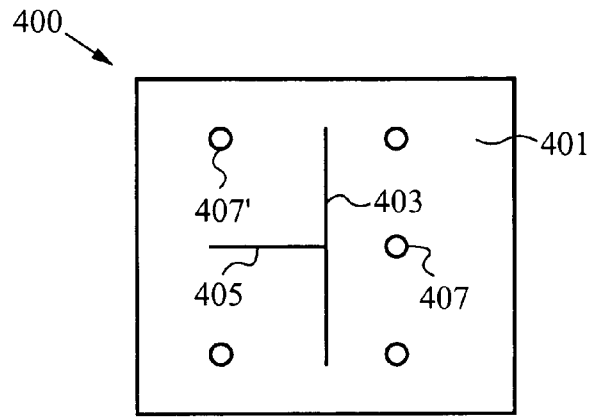
FIGS. 4A-M illustrate top views of portions of cleaning heads with squeegee elements, bristles and/or nodules, in accordance with the embodiments of the invention.

Referring now to FIG. 4A, a squeegee configuration 400, in accordance with the embodiments of the invention, comprises elongated squeegee segments 403 and 405 that intersect and provide top wiping edges and side wiping edges, as explained above. One, or both, of the elongated squeegee segments 403 and 405 protrude from a support surface 401 and can be surrounded or flanked by bristles and/or nodules 407 and 407' that also protrude from the support surface 401 and are preferably configured to wipe a working surface (not shown) simultaneously with the top wiping edges of the elongated squeegee segments 403 and 405.

Figure 4B:
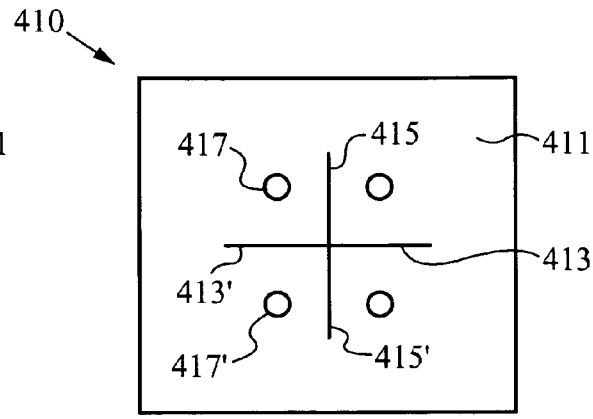

Referring now to FIG. 4B, a squeegee configuration 410, in accordance with the embodiments of the invention, comprises elongated squeegee segments 413, 413', 415 and 415' that intersect and provide top wiping edges that form a cross-shape with side wiping edges. One or more of the elongated squeegee segments 413, 413', 415 and 415' protrude from a support surface 411 and can be surrounded or flanked by bristles or nodules 417 and 417' that also protrude from the support surface 411 and are preferably configured to wipe a working surface (not shown) simultaneously with the top wiping edges of the elongated squeegee segments 413, 413', 415 and 415'.

Figure 4C:
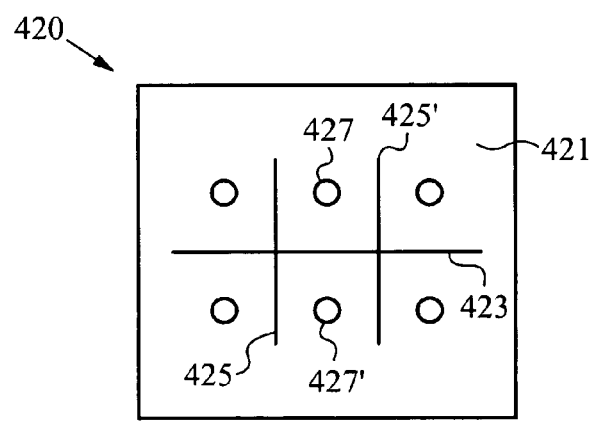

Referring now to FIG. 4C, a squeegee configuration 420, in accordance with the embodiments of the invention, comprises a major elongated squeegee segment 423 and a plurality of minor intersecting squeegee segments 425 and 425' that intersect with a wall of the major elongated squeegee segment 423 to provide cross-like top wiping edges and side wiping edges. One or more of the major squeegee segment 423 and the minor squeegee segments 425 and 425' protrude from a support surface 421 and can be surrounded or flanked by bristles and/or nodules 427 and 427' that also protrude from the support surface 421 and are preferably configured to wipe a working surface (not shown) simultaneously with the top wiping edges of the squeegee segments 423, 425 and 425'.

Figure 4D:
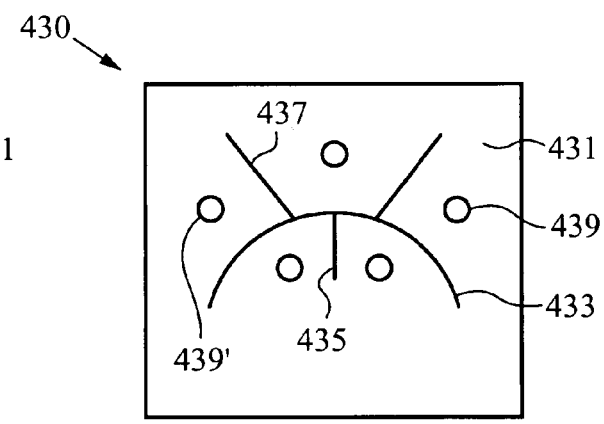

Referring now to FIG. 4D, a squeegee configuration 430, in accordance with the embodiments of the invention, comprises one or more curved squeegee segments 433 and a plurality intersecting squeegee segments 435 and 437. The intersecting squeegee segments 435 and 437 can extend from inside of the curvature of the squeegee segment 433, such as 435, or radiate outward from outside of the curvature of the squeegee segment 433, such as 437, to provide top wiping edges and side wiping edges. The curved squeegee segment 433 and the intersecting squeegee segments 435 and 437 protrude from a support surface 431 and can be surrounded or flanked by bristles and/or nodules 439 and 439' that also protrude from the support surface 431 and are preferably configured to wipe a working surface (not shown) simultaneously with the top wiping edges of the curved 433 and intersecting squeegee segments 435 and 437.

Figure 4E:
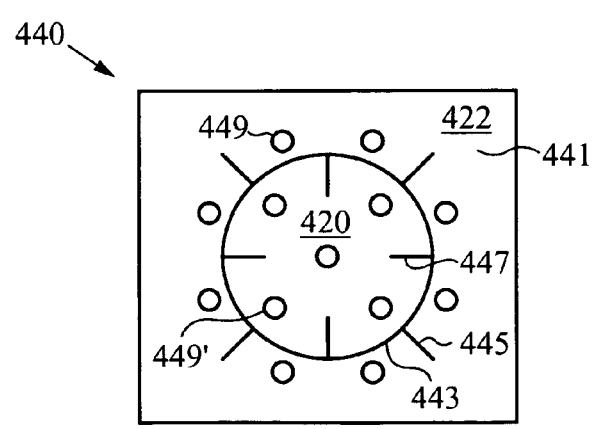

Referring now to FIG. 4E, a squeegee configuration 440, in accordance with the embodiments of the invention, comprises a curved and continuous squeegee segment 443 that forms or bounds an inner squeegee region 420 and an outer squeegee region 422. The squeegee configuration 440 can further comprise intersecting squeegee segments 447 that extend form an inside wall of the curved and continuous squeegee segment 443 and/or intersecting squeegee segments 445 that extend from an outer wall of the curved and continuous squeegee segment 443 to provide top wiping edges and side wiping edges. The curved and continuous squeegee segment 443 and the intersecting squeegee segments 445 and 447 protrude from a support surface 441 and can be surrounded or flanked by bristles and/or nodules 449 and 449' that also protrude from the support surface 441 and are preferably configured to wipe a working surface (not shown) simultaneously with the top wiping edges of the curved and continuous squeegee segment 443 and intersecting squeegee segments 445 and 447.

Figure 4F:
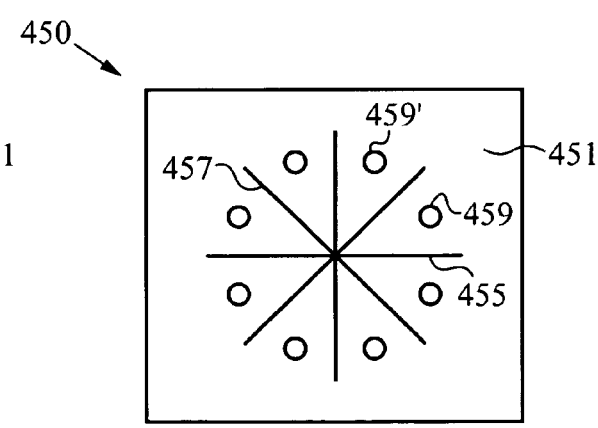

Referring now to FIG. 4F, a squeegee configuration 450, in accordance with the embodiments of the invention, comprises elongated squeegee segments 455 and 457 that intersect and extend at angles less than 90 degrees relative to each other and provide spoke-shaped top wiping edges and side wiping edges. The elongated squeegee segments 455 and 457 protrude from a support surface 451 and can be surrounded or flanked by bristles and/or nodules 459 and 459' that also protrude from the support surface 451 and are preferably configured to wipe a working surface (not shown) simultaneously with the top wiping edges of the elongated squeegee segments 455 and 457.

Figure 4G:
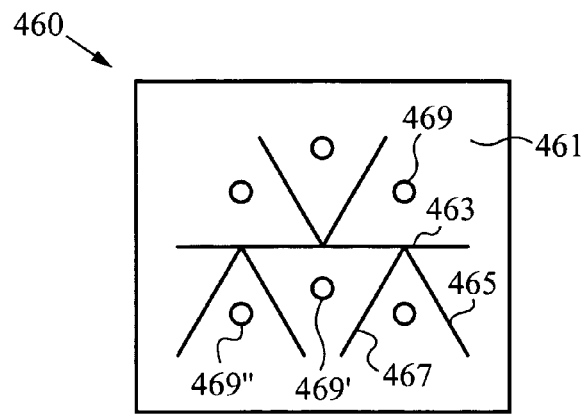

Referring now to FIG. 4G, a squeegee configuration 460, in accordance with the embodiments of the invention, comprises a major squeegee segment 463 and a plurality of minor and intersecting squeegee segments 465 and 467 that intersect a wall of the major squeegee segment 463 and extend from a wall of the major squeegee segment 463 at angles less than or greater than 90 degrees to provide top wiping edges and side wiping edges. The major squeegee segment 463 and the minor squeegee segments 465 and 467 can protrude from a support surface 461 and can be surrounded or flanked by bristles and/or nodules 469, 469' and 469" that also protrude from the support surface 461. The bristle or nodules 469, 469' and 469" are preferably configured to wipe a working surface (not shown) simultaneously with the top wiping edges of the squeegee segments 463, 465 and 467.

Figure 4H:
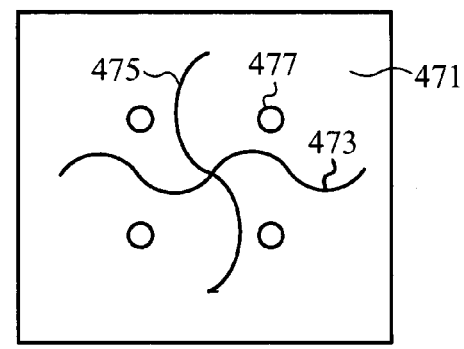

Referring now to FIG. 4H, a squeegee configuration 470, in accordance with the embodiments of the invention, comprises curved squeegee segments 473 and 475 that intersect and provide curved or wave-like top wiping edges and side wiping edges. One or more of the curved squeegee segments 473 and 475, or a portion thereof, protrude from a support surface 471 and can be surrounded or flanked by bristles and/or nodules 477 that also protrude from the support surface 471 and are preferably configured to wipe a working surface (not shown) simultaneously with the top wiping edges of the squeegee segments 473 and 475.

Figure 4I:
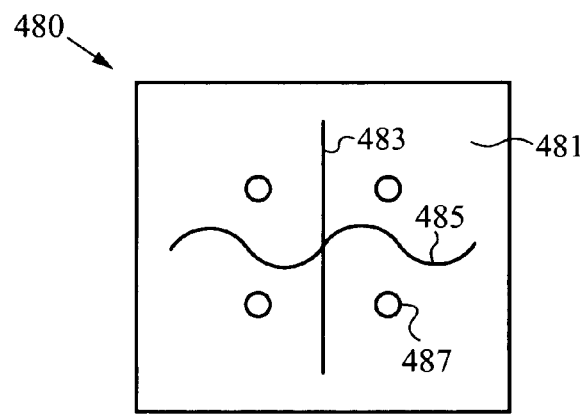

Referring now to FIG. 4I, a squeegee configuration 480, in accordance with the embodiments of the invention, comprises a linear squeegee segment 483 and a curved squeegee segment 485 that intersect and provide linear and curved top wiping edges and side wiping edges. One or more of the squeegee segments 483 and 485, or a portion thereof, protrude from a support surface 481 and can be surrounded or flanked by bristles and/or nodules 487 that also protrude from the support surface 481 and are preferably configured to wipe a working surface (not shown) simultaneously with the linear and curved top wiping edges of the squeegee segments 483 and 485.

Figure 4J:
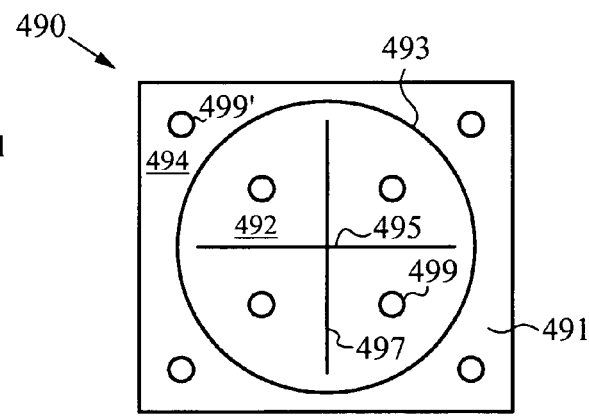

Referring now to FIG. 4J, a squeegee configuration 490, in accordance with the embodiments of the invention, comprises a continuous squeegee segment 493 that forms or bounds an inner squeegee region 492 and an outer squeegee region 494. The continuous squeegee segment 493 has a continuous top wiping edge that encircles or surrounds intersecting squeegee segments 495 and 497. The intersecting squeegee segments 495 and 497 provide cross-shaped top wiping edges and side wiping edges, as explained above. At least a portion of the continuous squeegee segment 493 and one or more of the intersecting squeegee segments 495 and 497 protrude from a support surface 491. Bristles and/or nodules can protrude from the support surface 491 corresponding to the inner squeegee region 492 (as with 499), the outer squeegee region 494 (as with 499') or both, such that the intersecting squeegee segments 495 and 497 and/or the continuous squeegee segment 493 are surrounded or flanked by bristles and/or nodules 499 and 499'. Preferably, the bristles and/or nodules 499 and 499' are configured to wipe a working surface (not shown) simultaneously with the top wiping edges of the squeegee segments 493, 495 and 497.

Figure 4K:
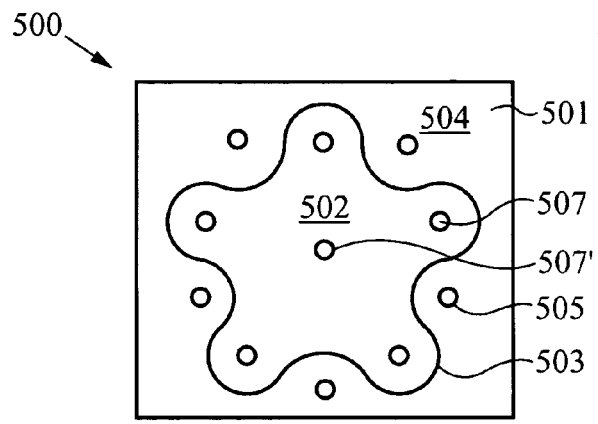

Referring now to FIG. 4K, a squeegee configuration 500, in accordance with the embodiments of the invention, comprises a continuous wave-shaped squeegee segment 503 that forms or bounds an inner squeegee region 502 and an outer squeegee region 504. The continuous wave-shaped squeegee segment 503 can be surrounded or flanked by bristle, bristle sections and/or nodules 505 and 507. Preferably, the bristle, bristle sections and/or nodules 505 and 507 are configured to move and contact a working surface (not shown) simultaneously with the top wiping edge of the continuous wave-shaped squeegee segment 503. Preferably, the squeegee configuration 500 includes an aperture 507' that is surrounded by the continuous wave-shaped squeegee segment 503 and is configured to dispense an oral-care solution, such as described above.

Figure 4L:
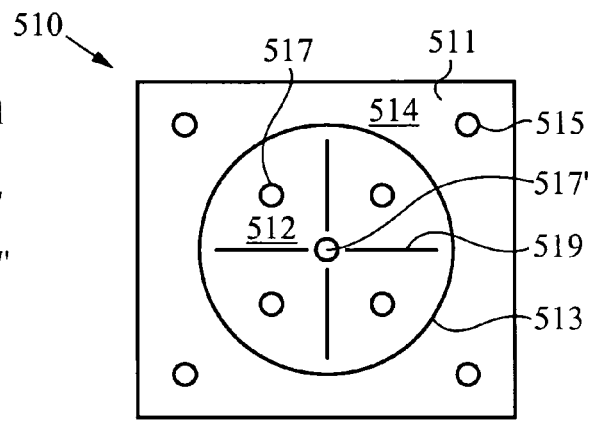

Referring now to FIG. 4L, a squeegee configuration 510, in accordance with the embodiments of the invention, comprises a continuous squeegee 513 that protrudes from a support surface 511 forms or bounds an inner squeegee region 512 and an outer squeegee region 514. The continuous squeegee can be surrounded or flanked by bristles, bristle sections and/or nodules 515 and 517. Preferably, the bristle, bristle sections and/or nodules 515 and 517 are configured to move and contact a working surface (not shown) simultaneously with the top wiping edge of the continuous squeegee 513. The squeegee configuration can also include squeegee segment 519 that protrudes from the inner squeegee region 512. Preferably, the bristles, bristle sections and/or nodules 515 and 517 are configured to wipe the working surface simultaneously with the top wiping edge of the continuous squeegee 513, while an oral-care solution is dispensed from a centrally located aperture 517 that is surrounded by the continuous squeegee 513.

Figure 4M:
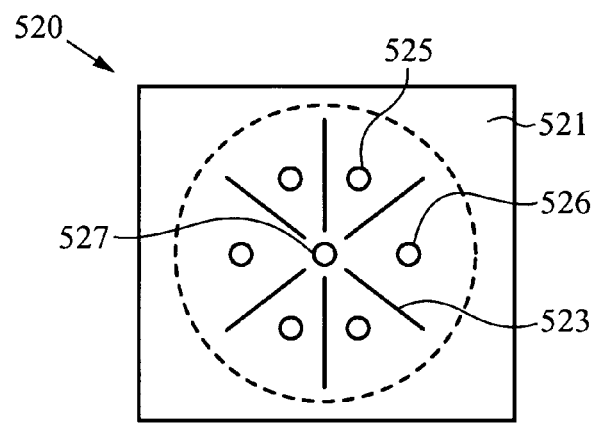

Referring now to FIG. 4M, a squeegee configuration 520, in accordance with the embodiments of the invention, comprises a plurality of squeegee segments 523 protruding form a support surface 521 and extending radially outward from a centrally located aperture 527 The squeegee segments can be surrounded or flanked by bristle, bristle sections and/or nodules 525 and 526. Preferably, the bristle, bristle sections and/nodules 525 and 526 are configured to move and contact a working surface (not shown) simultaneously with the top wiping edges of the squeegee segments 523.

Figure 5A:
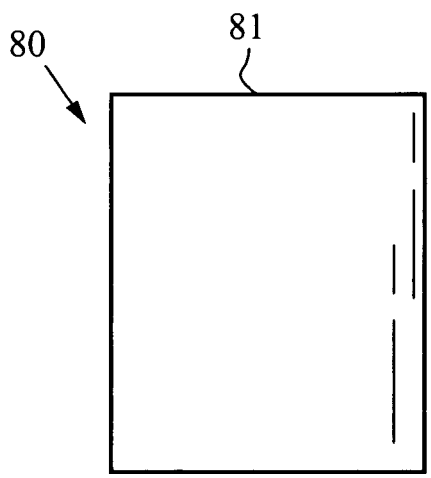
FIGS. 5A-F show several shaped or contoured squeegee edges, in accordance with the embodiments of the invention.
Figure 5B:
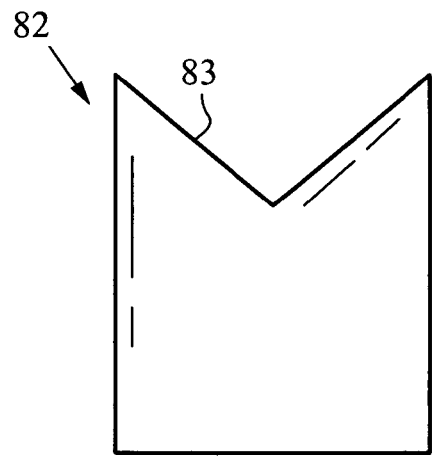
Figure 5C:
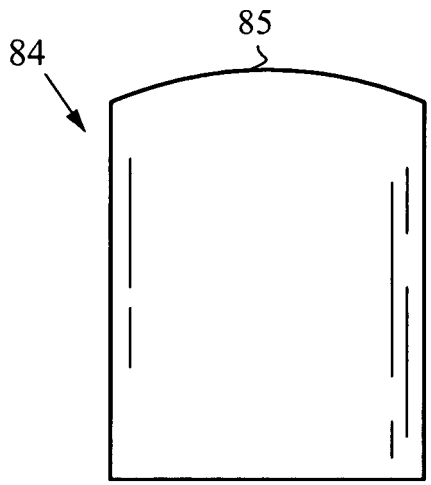
Figure 5D:
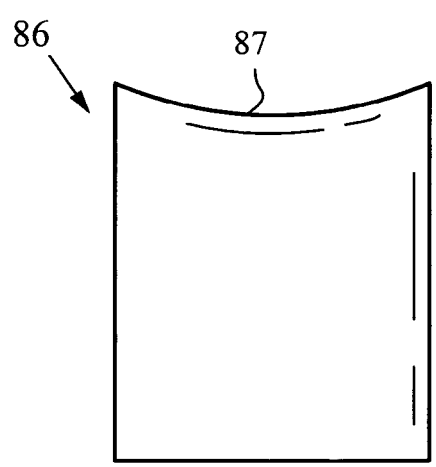
Figure 5E:
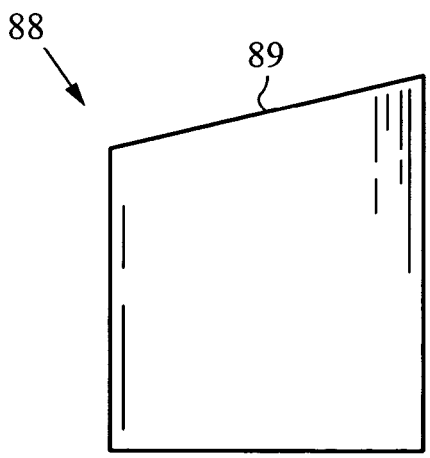
Figure 5F:
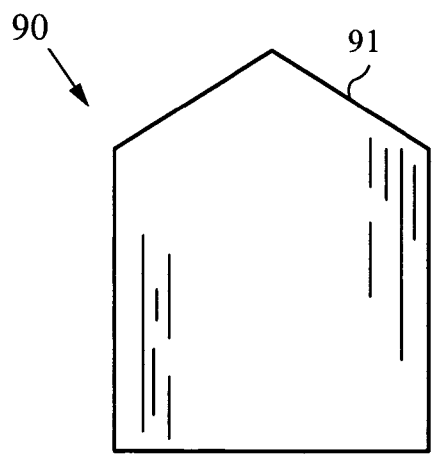

FIGS. 5A-F illustrate several shaped squeegee segments and/or partial structure or squeegee elements, used in the present invention. FIG. 5A shows a squeegee segment 80 with a planar contact edge 81; FIG. 5B shows a squeegee segment 82 with a V-shaped or notched contact edge 83; FIG. 5C shows a squeegee segment 84 with a curve convex contoured contact edge 85; FIG. 5D shows a squeegee segment 86 with a concave contoured contact edge 87; FIG. 5E shows a squeegee segment 88 with a diagonally contoured contact edge 89; and FIG. 5F shows a squeegee segment 90 with a pointed contact edge 91. The shaped squeegee segments described above can be combined in any number of ways to provide elongated squeegee wiping edges used in the oral cleaning device, system and method of the present invention.

Figure 6A:
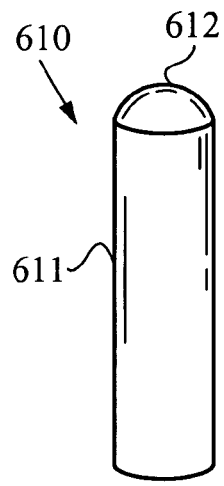
FIGS. 6A-H show nodule structures, in accordance with the embodiments of the invention.
Figure 6B:
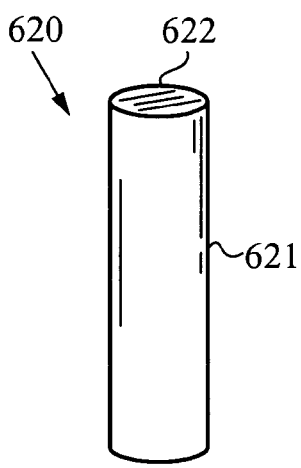
Figure 6C:
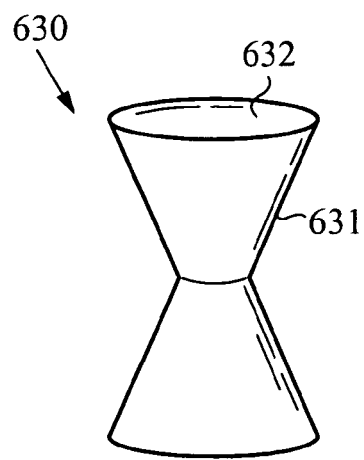
Figure 6D:
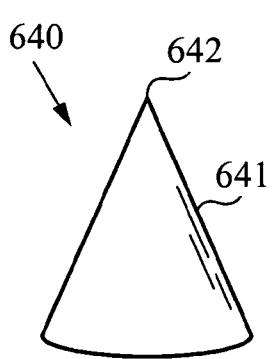
Figure 6E:
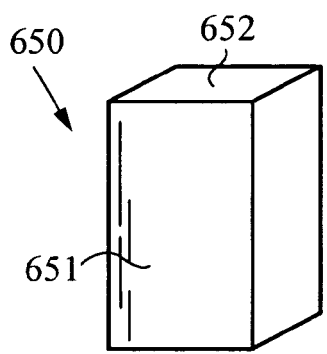
Figure 6F:
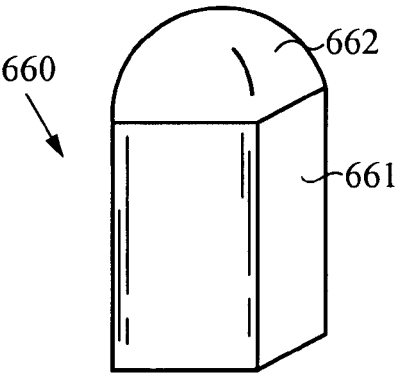
Figure 6G:
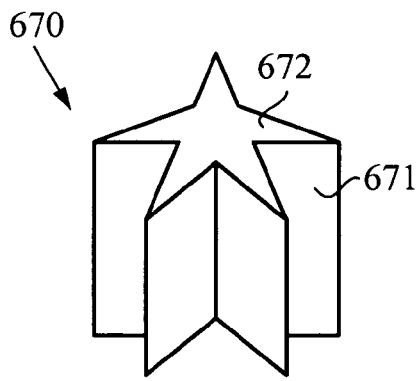
Figure 6H:
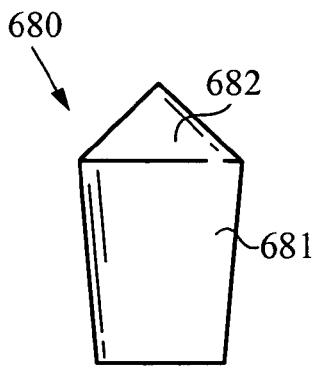

FIGS. 6A-H illustrate several symmetrical nodule structure geometries that are useful in contact devices of the present invention. FIG. 6A shows a nodule 610 with cylindrical protruding walls 611 and a rounded tip portion 612; FIG. 6B shows a nodule 620 with cylindrical protruding walls 621 and a flat top 622; FIG. 6C shows a nodule 630 with contoured protruding walls 631 and a flat top 632; FIG. 6D shows a pointed nodule 660 with tapered protruding walls 641 and a tip 642; FIG. 6E shows a rectangular nodule 650 with planar walls 651 and a flat top 652; FIG. 6F shows a nodule 660 with planar walls 661 and a rounded tip portion 662; FIG. 6G shows a star shaped nodule 670 with protruding walls 671 and a star-shaped top 672; and FIG. 6H shows a triangular nodule 680 with protruding walls 681 and triangular-shaped top 682.

Figure 7A:
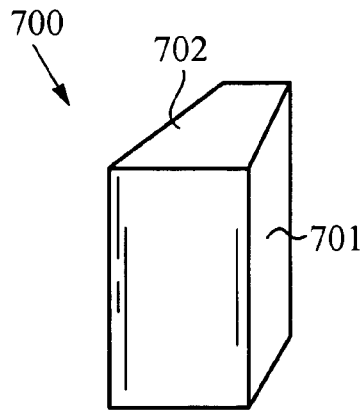
FIGS. 7A-G show alternative nodule structures, in accordance with the embodiments of the invention.
Figure 7B:
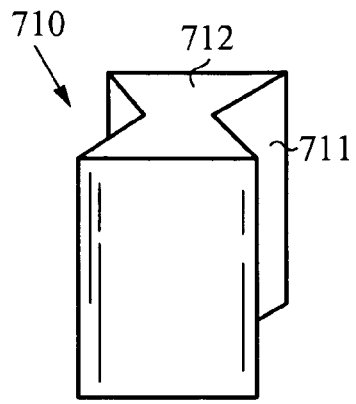
Figure 7C:
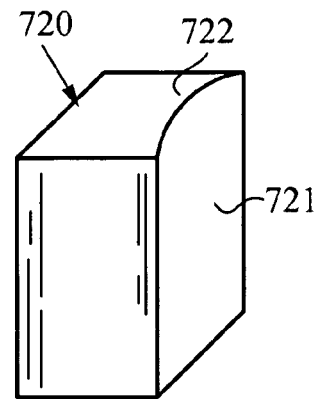
Figure 7D:
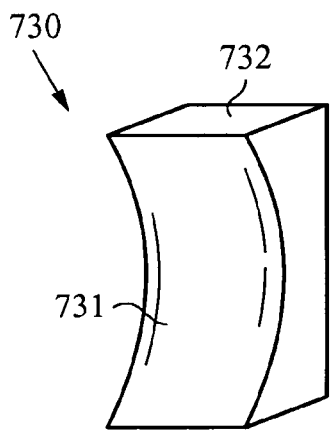
Figure 7E:
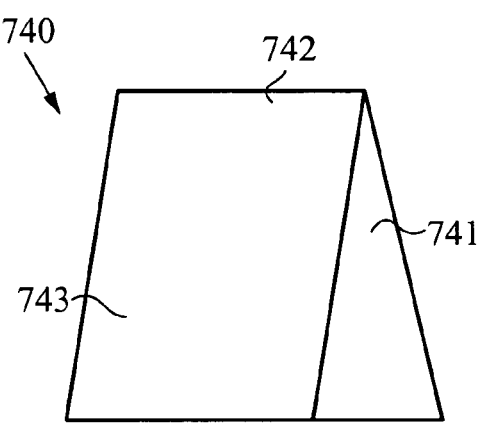
Figure 7F:
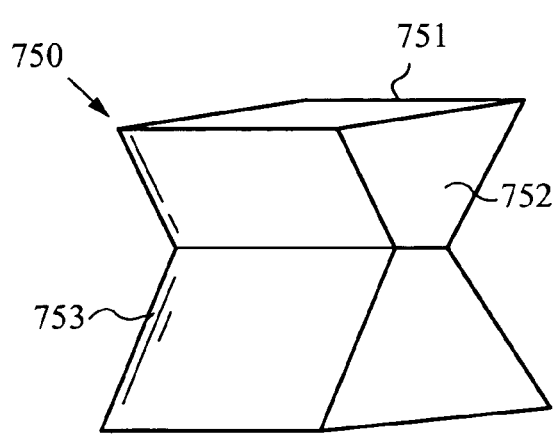
Figure 7G:
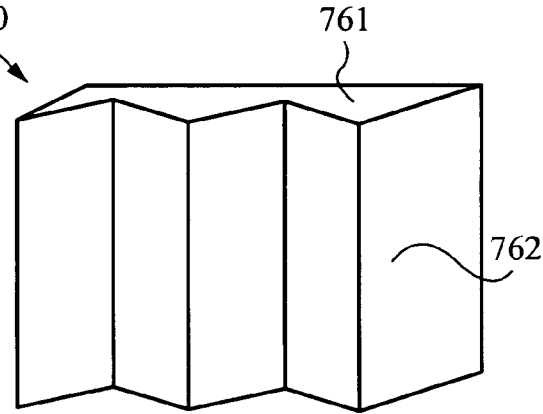

FIGS. 7A-G illustrate several asymmetrical nodule structure geometries that are useful in contact device of the present invention. FIG. 7A shows a wedge-shaped nodule 700 with protruding walls 701 and a top 702; FIG. 7B shows a nodule 710 with contoured walls 711 and a bow-tie shaped top 712; FIG. 7C shows a curved nodule 720 with protruding walls 721 (curved in the elongation direction) and a flat top 722; FIG. 7D shows a curved nodule 730 with protruding walls 731 (curved in the protruding direction) and a top 732; FIG. 7E shows a wedge shaped nodule 740 with tapered walls 743, triangular walls 741 and an edge 742; FIG. 7F shows a nodule 750 with grooved walls 753, bow-tie shaped walls 752 and a flat top 751; and FIG. 7G shows a nodule 760 with contoured walls 762 and a top 761. It will be clear to one skilled in the art that any number of symmetric and asymmetric nodule geometries and combinations thereof are useful in the contact device of the instant invention. Further descriptions of nodule structures and their applications are described in U.S. Pat. No. 6,865,767, referenced previously.

Figure 8:
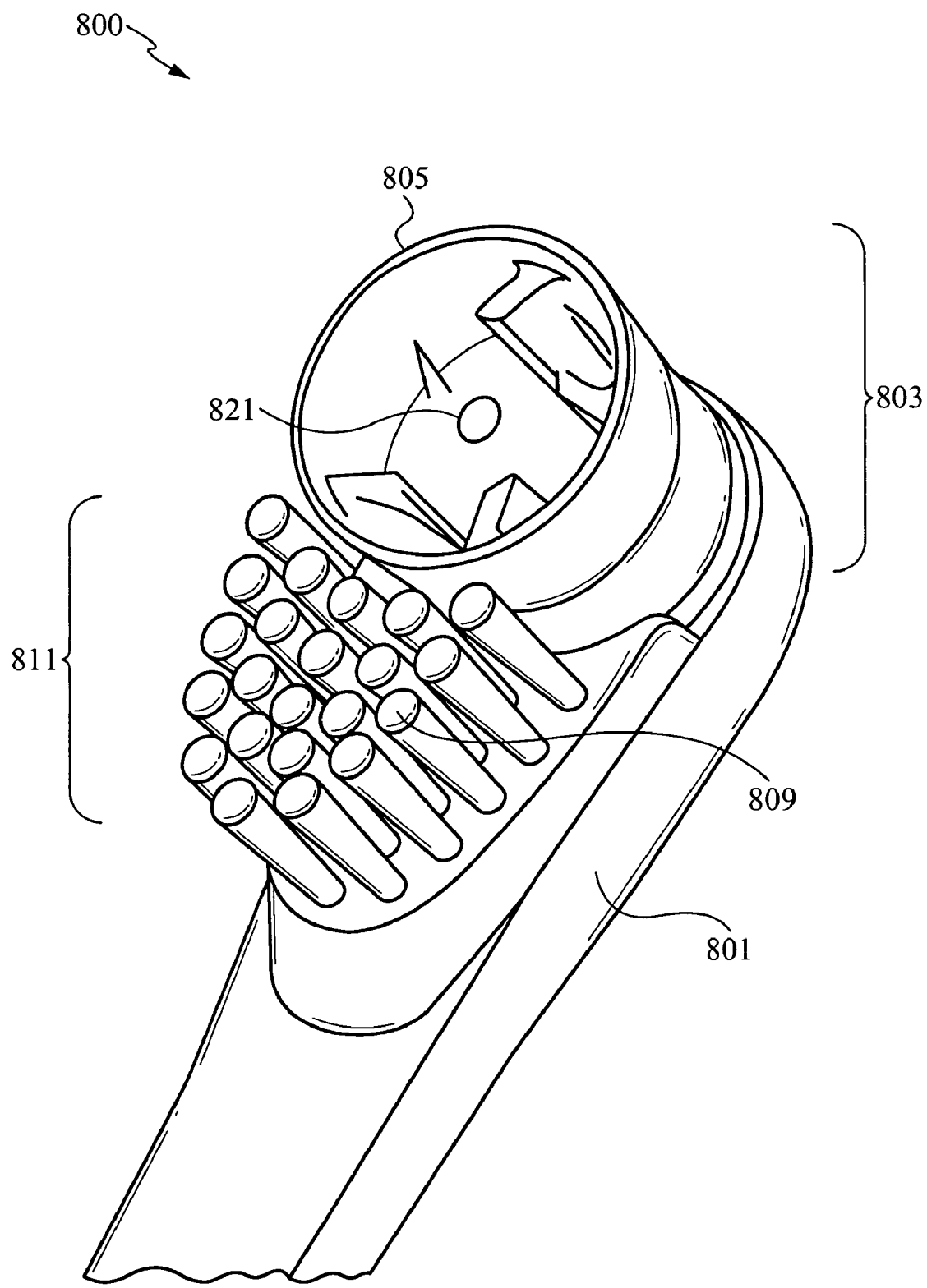
FIG. 8 shows a perspective view of a power head of an oral-care cleaning apparatus, in accordance with the embodiments of the invention.

FIG. 8 shows an oral-care cleaning head 800, in accordance with a preferred embodiment of the invention. The oral-care cleaning head 800 comprises a support structure 801 for supporting a first region 811 and a second region 803. The first region 811 comprises bristle tufts 809 for wiping the surfaces of gums and teeth. The second region 803 comprises a cup-shaped squeegee element 805 that includes a continuous squeegee segment encircling a portion of the second region 803 and squeegee fins protruding from an inner wall of the continuous squeegee segment. The continuous squeegee segment preferably encircles at least one aperture that is configured to dispense an oral-care solution while the cup-shaped squeegee element 805 rotates, oscillates or otherwise move.

The first region 811 can be configured to remain stationary or move in any number of ways, as described above, while cleaning teeth and gums. Preferably the cup-shaped squeegee element 805 and the bristle tufts 807 of the second region 803 are configured to oscillate and/or rotate while cleaning teeth and/or gums. The oral-care cleaning head 800, described above is most preferably configured to detachably couple to a power handle, such as described with reference to FIG. 2.

Figure 9A:
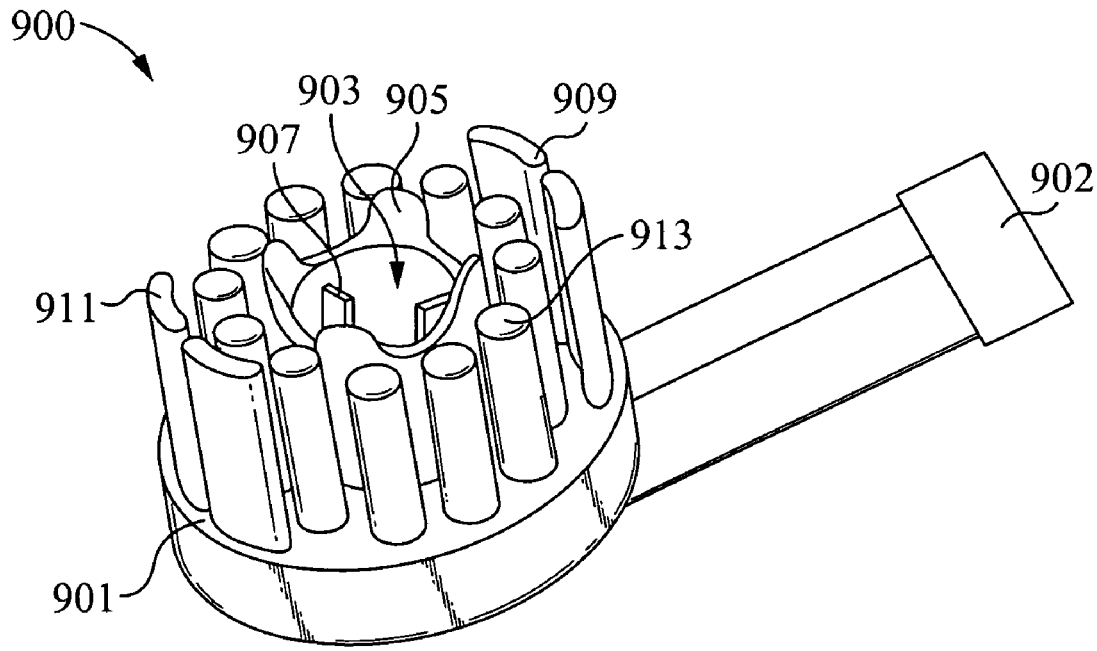
FIGS. 9A-9D show perspective views of cleaning head configurations with prophy-cup polishing elements, bristle tufts and/or nodule polishing elements, in accordance with further embodiments of the invention.

FIGS. 9A-9D show perspective views of cleaning head configurations with prophy-cup polishing elements, bristle tufts and/or nodule polishing elements, in accordance with further embodiments of the invention. Referring to FIG. 9A, the cleaning head 900 includes a prophy-cup polishing element 903 protruding from a movable support 901. The prophy-cup polishing element 903 includes an aperture surrounded by corrugated or contoured polishing edge 905. The aperture is configured for dispensing an oral-care solution, while the prophy-cup polishing element 903 rotates or oscillates. The prophy-cup polishing element 903 also has a plurality of wiping fins 907 extending inward from an inner wall of the prophy-cup polishing element 903. The cleaning head 900 also includes a plurality of bristle tufts and/or nodule polishing elements 913 protruding from the movable support 901 and surrounding the prophy-cup polishing element 903. The cleaning head 900 can also include curved squeegee polishing elements or curved bristle tufts 909 and 911.

Figure 9B:
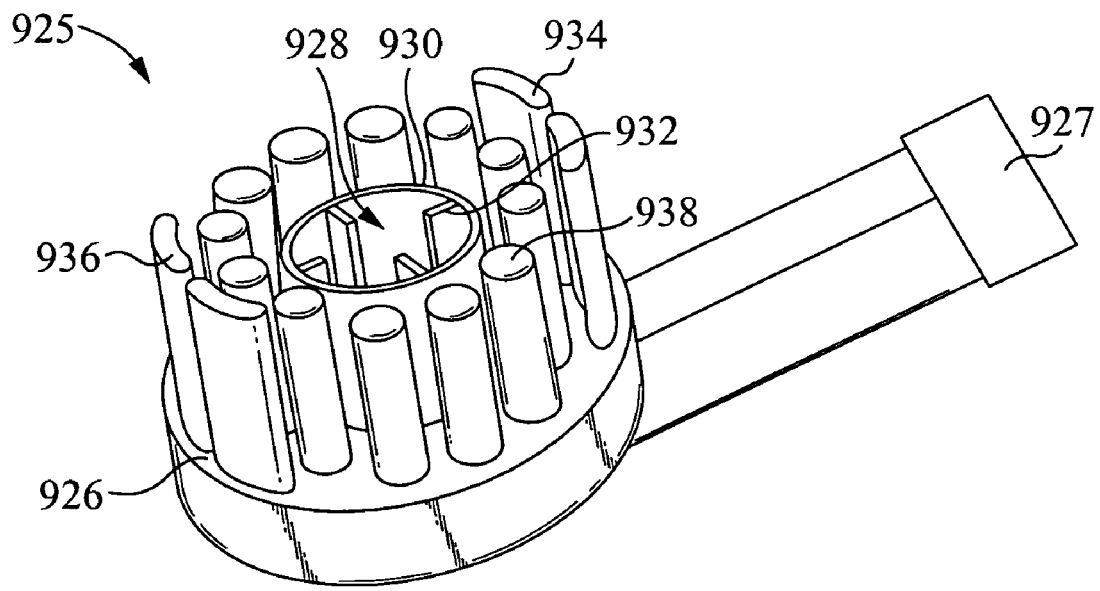

FIG. 9B shows a cleaning head 925 that includes a prophy-cup polishing element 928 protruding from a movable support 926. The prophy-cup polishing element 928 has a continuous polishing edge 930 and a plurality of wiping fins 932 extending inward from an inner wall of the prophy-cup polishing element 928. The cleaning head 925 also includes a plurality of bristle tufts and/or nodule polishing elements 938 protruding from the movable support 926 and surrounding prophy-cup polishing element 928. The prophy-cup polishing element 928 includes an aperture surrounded by the continuous polishing edge 930 that is configured for dispensing an oral-care solution, while the prophy-cup polishing 928 element rotate or oscillates. The cleaning head 925 can also include curved squeegee polishing elements or curved bristle tufts 934 and 936.

Figure 9C:
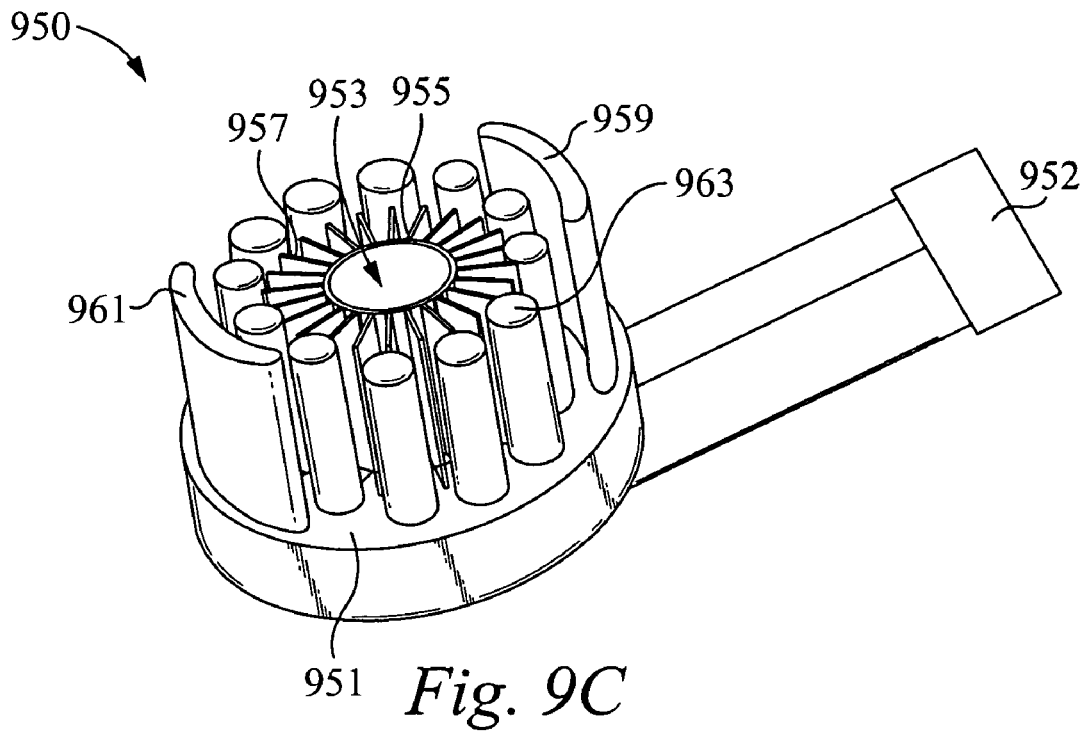

FIG. 9C shows a cleaning head 950 that includes a prophy-cup polishing element 953 protruding from a movable support 951. The prophy-cup polishing element 953 has a continuous polishing edge 955 and a plurality of wiping fins 957 that extend outward from an outer wall of the prophy-cup polishing element 953. The prophy-cup polishing element 953 also includes an aperture surrounded by the continuous polishing edge 955 for dispensing and oral-care solution, while the prophy-cup polishing element rotates or oscillates. The cleaning head 950 also includes a plurality of bristle tufts and/or nodule polishing elements 963 protruding from the movable support 951 and surrounding prophy-cup polishing element 953. The cleaning head 950 can also include curved squeegee polishing elements or curved bristle tufts 959 and 961.

Figure 9D:
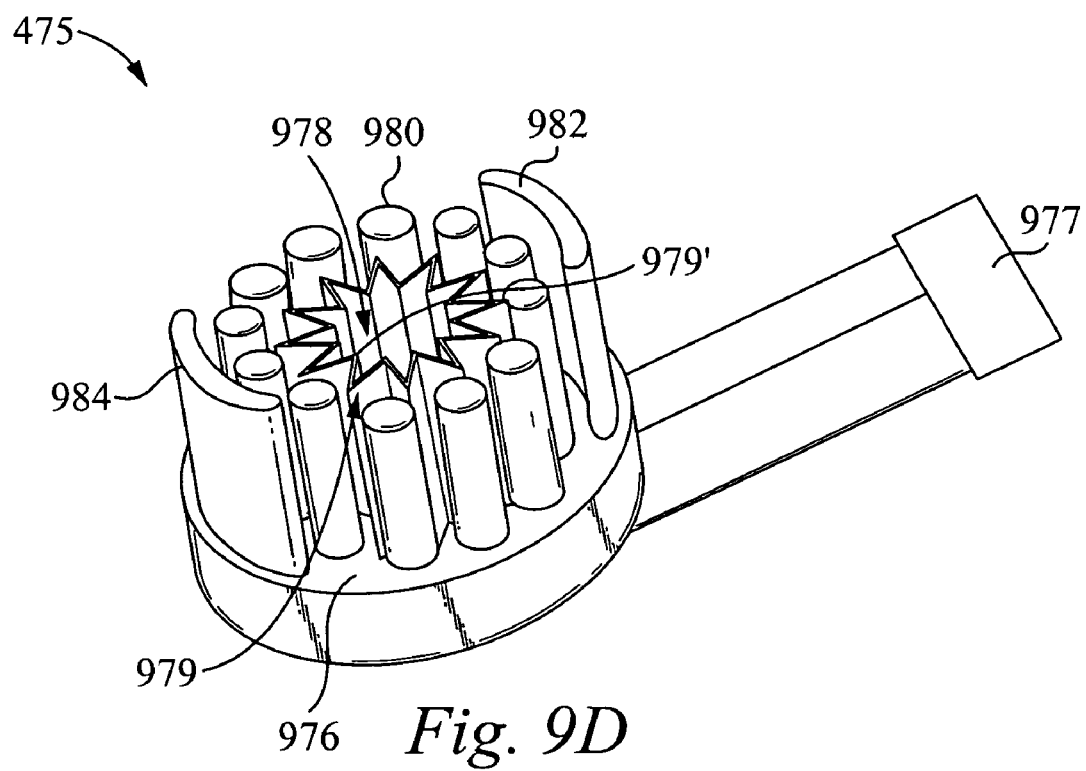

FIG. 9D shows a cleaning head 975 that includes a prophy-cup polishing element 978 protruding from a movable support 976. The prophy-cup polishing element 978 has corrugated or angled walls 979 and 979' that provides a zig zag-like top wiping edge. The prophy-cup polishing element 978 includes an aperture surrounded zig zag-like top wiping edge that is configured to dispense an oral-care solution, while the prophy-cup polishing element 978 rotates or oscillates. The cleaning head 975 also includes a plurality of bristle tufts and/or nodule polishing elements 980 protruding from the movable support 976 and surrounding prophy-cup polishing element 978. The cleaning head 978 can also include curved squeegee polishing elements or curved bristle tufts 982 and 984. Each of the cleaning heads 900, 925, 950 and 975 can include an attachment means 902, 927, 952 and 977, respectfully, for detachably coupling the cleaning heads 900, 925, 950 and 975 to a motorized handle, such as described with reference to FIG. 2A. Also the nodule polishing elements and curved squeegee elements described above can have any number of geometric shapes that include contoured or shaped walls, wiping edges and/or tips, such as described with reference to FIGS. 5A-F, 6A-6H and 7A-7G. Also, the prophy-cup polishing elements, the nodule polishing elements, the curved squeegee elements and the bristle tufts can protrude form the moving supports to any suitable height or combination of heights. Further, the wiping fins can have any number of different geometries that include shaped or contoured walls or tips.

It will be clear to one skilled in the art from the description above that top wiping edges and side wiping edges of the squeegee element and segments described can be contoured, corrugated, curved, pointed, angled, tapered or otherwise textured. While embodiments have been described with bristles, bristles are not required. Further, any number of the features described above can be combined in different ways to provide other squeegee configurations that are considered to be within the scope of the invention. It is also understood that an abrasive material can be integral with the squeegee segments or attached to the walls or edges of squeegees as required for the application at hand. Further, it is understood that the squeegee configurations, in accordance with the embodiments of the invention, can include absorbent elements, such as sponge elements, and abrasive elements, such as scouring elements that are separate from the squeegee segments. Also, walls of squeegee segments, while generally shown as uniform herein, can vary in thickness in either an elongated direction, in a protruding direction or both. Accordingly, the proceeding preferred embodiments of the invention are set forth without any loss of generality to, and without imposing limitations upon, the claimed invention.

What is claimed is:

1. A device comprising a cleaning head, the cleaning head comprising:
   a) a first region with a first squeegee element with at least two elongated solid walls forming a corresponding elongated top wiping edge configured to treat a working surface; and
   b) a second region with bristles configured to simultaneously treat the working surface; and
   c) means for delivering a solution through one or more apertures on the cleaning head, wherein at least one of the first region and the second region is configured to move with a rotation motion relative to a stationary handle and relative to the other of the at least one of the first region and the second region.

2. The device of claim 1, wherein the second region further comprises a second squeegee element.

3. The device of claim 2, wherein the second squeegee element comprises at least two terminus ends that form side wiping edges.

4. The device of claim 1, wherein the first region further comprises bristles.

5. The device of claim 1, wherein the at least one of the first region and second region is further configured to vibrate.

6. The device of claim 1, wherein the first squeegee element comprises at least two terminus ends that form side wiping squeegee edges.

7. The device of claim 1, wherein the first squeegee element encircles an inner squeegee region.

8. The device of claim 1, further comprising a motorized handle configured to detachably couple the cleaning head.

9. The device of claim 1, wherein a portion of the first squeegee element is corrugated, rounded, angled or pointed.

10. The device of claim 1, further comprising nodules protruding from the cleaning head.

11. A device comprising a motorized cleaning head comprising:
    a) a support structure with one or more apertures for dispensing an oral-car liquid;
    b) a squeegee member with at least two elongated solid walls forming a corresponding elongated top wiping edge protruding from a first portion of the support member; and
    c) bristles protruding from a second portion support member, wherein at least the first portion of the support structure is configured to move relative to a stationary handle coupled thereto and relative to the second portion of the support structure.

12. The device of claim 11, wherein the at least two elongated solid walls are curved.

13. The device of claim 11, wherein the first portion of the support member is configured to vibrate, rotate or oscillate.

14. The device of claim 11, wherein the squeegee member further comprises a plurality of fin structures.

15. The device of claim 11, wherein the first portion of the support member comprises bristles and wherein one of the at least two elongated squeegee walls encircles at least a portion of the bristles.

16. The device of claim 11, further comprising nodules protruding from at least one of the first portion and second portion of the support member.

17. The device of claim 11, wherein the second portion of the support member is configured to vibrate, rotate or oscillate.

18. A device comprising a cleaning head comprising:
    a) a first region with an aperture for dispensing a solution and a continuous squeegee that has solid walls that surround the aperture and form a continuous top wiping edge; and
    b) a second region with bristles, wherein the continuous squeegee is configured to a rotate or oscillate relative to the second region.

19. The device of claim 18, wherein the second region further comprises a squeegee wiping element.

20. The device of claim 18, further comprising one or more nodules.

21. The device of claim 18, further comprising a handle for moving at least one of the first region and the second region.

22. The device of claim 21, further comprising a pump mechanism for delivering an oral-care solution to the cleaning head through the aperture.

23. A device comprising:
   a) a cleaning head with one or more squeegees and bristles protruding from a first support surface with one or more apertures, wherein each of the one or more squeegees have at least two elongated solid walls forming a corresponding elongated top wiping edge;
   b) a power handle configured to move the first support surface and configured to dispensing pulses of a liquid through the one or more apertures, while the first support surface moves with a rotational motion relative to a stationary handle; and
   c) a second support surface comprising one or more squeegees have at least two elongated solid walls forming a corresponding elongated top wiping edge and or bristles.

* * * * *